United States Patent
Donald et al.

(10) Patent No.: US 12,024,725 B2
(45) Date of Patent: Jul. 2, 2024

(54) COMPOSITIONS FOR INHIBITING KRas SIGNALING AND METHODS OF MAKING AND USING SAME

(71) Applicant: Duke University, Durham, NC (US)

(72) Inventors: Bruce Donald, Durham, NC (US);
Anna Lowegard, Durham, NC (US);
Marcel Frenkel, Durham, NC (US)

(73) Assignee: Duke University, Durham, NC (US)

( * ) Notice: Subject to any disclaimer, the term of this patent is extended or adjusted under 35 U.S.C. 154(b) by 189 days.

(21) Appl. No.: 17/332,338

(22) Filed: May 27, 2021

(65) Prior Publication Data

US 2021/0371832 A1 Dec. 2, 2021

Related U.S. Application Data

(60) Provisional application No. 63/030,975, filed on May 28, 2020.

(51) Int. Cl.
| | |
|---|---|
| *C12N 9/12* | (2006.01) |
| *A61K 38/00* | (2006.01) |
| *A61K 47/66* | (2017.01) |
| *G06N 7/01* | (2023.01) |
| *G16B 15/00* | (2019.01) |
| *G16B 30/00* | (2019.01) |

(52) U.S. Cl.
CPC ............... *C12N 9/12* (2013.01); *A61K 38/00* (2013.01); *A61K 47/66* (2017.08); *C12Y 207/11001* (2013.01); *G06N 7/01* (2023.01); *G16B 15/00* (2019.02); *G16B 30/00* (2019.02)

(58) Field of Classification Search
CPC .......... A61K 38/00; A61K 47/66; C12N 9/12; C12Y 207/11001
See application file for complete search history.

(56) References Cited

PUBLICATIONS

NP_001341622.1, NCBI, protein database, RAF proto-oncogene serine/threonine-protein kinase isoform d [*Homo sapiens*], NCBI Reference Sequence : NP_001341622.1 (Updated Mar. 18, 2023), also available at https://www.ncbi.nlm.nih.gov/protein/NP_001341622.1 (last visited May 10, 2023) (Year: 2016).*
NP_001341618.1, NCBI, protein database, RAF proto-oncogene serine/threonine-protein kinase isoform a [*Homo sapiens*], NCBI Reference Sequence : NP_001341618.1 (Updated Mar. 17, 2023; first reported in 1991, also available at https://www.ncbi.nlm.nih.gov/protein/NP_001341618.1 (last visited May 10, 2023). (Year: 2023).*

(Continued)

*Primary Examiner* — Randall L Beane
(74) *Attorney, Agent, or Firm* — Casimir Jones, S.C.; Rikki A. Hullinger

(57) ABSTRACT

In some aspects, provided herein are computational methods for structure-based protein design. These new methods and incorporated algorithms speed-up computational structure-based protein design while maintaining accurate calculations, allowing for larger, previously infeasible protein designs. In another aspect, provided herein are mutant c-RAF proteins, and conjugates comprising the same. The conjugates may be used in methods of treating cancer in a subject, such as in methods of treating a KRas mutant cancer.

4 Claims, 12 Drawing Sheets

(56) References Cited

PUBLICATIONS

NP_001341619.1, NCBI, protein database, RAF proto-oncogene serine/threonine-protein kinase isoform b [*Homo sapiens*], NCBI Reference Sequence : NP_001341619.1 (Updated Mar. 18, 2023), also available at https://www.ncbi.nlm.nih.gov/protein/NP_001341619.1(last visited May 10, 2023) (Year: 2016).*
Campbell-Valois FX et al., Massive sequence perturbation of a small protein, Proc Natl Acad Sci U S A, vol. 102(42):14988-93, and 14 pages of Supporting Data (Oct. 18, 2005) (Year: 2005).*
Lowegard et al., Novel, provable algorithms for efficient ensemble-based computational protein design and their application to the redesign of the c-Raf-RBD:KRas protein-protein interface, bioRxiv, doi: https://doi.org/10.1101/790949, 44 pages (Oct. 2, 2019) (Year: 2019).*
Campbell-Valois, Application des librairies de codons dégénérés à l'étude du mécanisme de repliement et de la stabilisation de la structure du domaine liant ras de Raf, Dissertation, University of Montreal, Department of Molecular Biology, 396 pages (Dec. 2005); in French (Year: 2005).*
Machine Translation by Google of Campbell-Valois, Dissertation entitled [Application of degenerate codon libraries to the study of the mechanism of folding and stabilization of the ras binding domain structure of Raf], University of Montreal, Dept. of Mol. Biol., 396 p., trans. May 10, 2023 (Year: 2023).*
Lowegard et al., (Predicting the Effect of Mutations in the KRas/c-Raf-RBD Protein-Protein Interface, Biophysical Journal, vol. 114(3) Supp 1 (Feb. 2, 2018) at p. 576a (Year: 2018).*
Block, C. et al. Quantitative structure-activity analysis correlating Ras/Raf interaction in vitro to Raf activation in vivo. Nature structural biology, 3(3):244, 1996.
Borrelli, et al., Cell Penetrating Peptides as Molecular Carriers for Anti-Cancer Agents. Molecules 2018, 23, 295, 1-28.
Campbell-Valois, F.-X. et al., Massive sequence perturbation of a small protein. Proceedings of the National Academy of Sciences, 102(42):14988-14993, 2005.
Campbell-Valois, F.X. et al., Massive sequence perturbation of the Raf Ras binding domain reveals relationships between sequence conservation, secondary structure propensity, hydrophobic core organization and stability. Journal of molecular biology, 362(1):151-171, 2006.
Chazelle, B et al. A semidefinite programming approach to side chain positioning with new rounding strategies. NForms Journal on Computing, 16(4):380-392, 2004.
Chen, C.-Y. et al., Computational structure-based redesign of enzyme activity. Proc Natl Acad Sci U S A, 106(10):3764-9, 2009.
Dahiyat, B. I. et al., De novo protein design: fully automated sequence selection. Science, 278(5335):82-7, 1997.
Delano, W. L. The PyMOL molecular graphics system. http://www.pymol.org, 2002.
Derakhshankhah, Cell penetrating peptides: A concise review with emphasis on biomedical applications. Biomed Pharmacother. Dec. 2018;108:1090-1096.
Donald, B.R. Algorithms in Structural Molecular Biology. MIT Press, Cambridge, MA, 2011.
Evaluating the safety and serum concentrations of a human monoclonal antibody, VRC-HIVMAB075-00-AB (VRC07-523LS), administered in multiple doses and routes to healthy, HIV-uninfected adults. clinicaltrials.gov identifier: nct03387150. niaid and national institutes of health clinical center. Sep. 2018.
Fetics, S. K. et al., Allosteric effects of the oncogenic RasQ61L mutant on Raf-RBD. Structure, 23(3):505-516, 2015.
Filchtinski, D. et al. What makes Ras an efficient molecular switch: a computational, biophysical, and structural study of Ras-GDP interactions with mutants of Raf. Journal of molecular biology, 399(3):422-435, 2010.
Frey, K. M. et al., Predicting resistance mutations using protein design algorithms. Proc Natl Acad Sci U S A, 107(31):13707-12, 2010.
Fridman, M. et al., c-Raf-1 RBD associates with a subset of active vH-Ras. Biochemistry, 39(50):15603-15611, 2000.
Fridman, M. et al., Point mutants of c-raf-1 RBD with elevated binding to v-Ha-Ras. Journal of Biological Chemistry, 275(39):30363-30371, 2000.
Fridman, M. et al., The minimal fragments of c-Raf-1 and NF1 that can suppress v-Ha-Ras-induced malignant phenotype. Journal of Biological Chemistry, 269(48):30105-30108, 1994.
Gainza, P. et al., Protein design using continuous rotamers. PLoS Comput Biol, 8(1):e1002335, 2012.
Gainza, P., et al., H. M. Nisonoff, and B. R. Donald. Algorithms for protein design. Current Opinion in Structural Biology, 39:16-26, 2016.
Gainza, P., et al., OSPREY: protein design with ensembles, flexibility, and provable algorithms. Methods Enzymol, 523:87-107, 2013.
Georgiev, I. et al., Algorithm for backrub motions in protein design. Bioinformatics, 24(13):i196-204, 2008.
Georgiev, I. et al., Dead-end elimination with backbone flexibility. Bioinformatics, 23(13):1185-94, 2007.
Georgiev, I. et al., Design of epitope-specific probes for sera analysis and antibody isolation. Retrovirology, 9, 2012.
Georgiev, I. et al., Improved pruning algorithms and divide-and-conquer strategies for dead-end elimination, with application to protein design. Bioinformatics, 22(14):e174-83, 2006.
Georgiev, I. et al., The minimized dead-end elimination criterion and its application to protein redesign in a hybrid scoring and search algorithm for computing partition functions over molecular ensembles. J Comput Chem, 29(10):1527-42, 2008.
Georgiev, I. S. et al. Antibodies VRC01 and 10E8 neutralize HIV-1 with high breadth and potency even with IG-framework regions substantially reverted to germline. J Immunol, 192(3):1100-6, 2014.
Gilson, M. K. et al., The statistical-thermodynamic basis for computation of binding affinities: a critical review. Biophys J, 72(3):1047-69, 1997.
Gorczynski, et al., Allosteric inhibition of the protein-protein interaction between the leukemia-associated proteins Runx1 and CBFbeta. Chem Biol, 14(10):1186-97, 2007.
Gorman, C. et al., Equilibrium and kinetic measurements reveal rapidly reversible binding of Ras to Raf. Journal of Biological Chemistry, 271(12):6713-6719, 1996.
Habault, et al. Recent Advances in Cell Penetrating Peptide-Based Anticancer Therapies. Molecules. Mar. 7, 2019;24(5):927.
Hallen, et al., OSPREY 3.0: open-source protein redesign for you, with powerful new features. Journal of Computational Chemistry, 39(30):2494-2507, 2018.
Hallen, M. A. et al., COMETS (constrained optimization of multistate energies by tree search): a provable and efficient protein design algorithm to optimize binding affinity and specificity with respect to sequence. Journal of Computational Biology, 23(5):311-321, 2016.
Hallen, M. A. et al., Compact representation of continuous energy surfaces for more efficient protein design. J Chem Theory Comput, 11(5):2292-306, 2015.
Hallen, M. A. et al., LUTE (local unpruned tuple expansion): accurate continuously flexible protein design with general energy functions and rigid-rotamer-like efficiency. Research in Computational Molecular Biology (RECOMB), 9649:122-136, 2016.
Hallen, M. A. et al., Protein design by algorithm. Communications of the ACM, 62(10), Oct. 2019; 76-84.
Hallen, M.A., et al. Dead-end elimination with perturbations (DEEPer): a provable protein design algorithm with continuous sidechain and backbone flexibility. Proteins, 81(1):18-39, 2013.
Hallen, M.A., et al., CATS (coordinates of atoms by taylor series): protein design with backbone flexibility in all locally feasible directions. Bioinformatics, 33(14):i5-i12, 2017.
Hastings, W. K. Monte carlo sampling methods using markov chains and their applications. Biometrika, 1970.
Herrmann, C. et al. Quantitative analysis of the complex be-tween p21 and the ras-binding domain of the human raf-1 protein kinase. Journal of Biological Chemistry, 270(7):2901-2905, 1995.
Herrmann, C. et al., Differential interaction of the ras family GTP-binding proteins H-Ras, Rap1A, and R-Ras with the putative

(56) References Cited

PUBLICATIONS effector molecules Raf kinase and Ral-guanine nucleotide exchange factor. Journal of Biological Chemistry, 271(12):6794-6800, 1996.

Hunter, J. C. et al. In situ selectivity profiling and crystal structure of SML-8-73-1, an active site inhibitor of oncogenic K-Ras G12C. Proceedings of the National Academy of Sciences, 111(24):8895-8900, 2014.

Hunter, J. C. et al., Bio-chemical and structural analysis of common cancer-associated KRAS mutations. Molecular cancer research, 13(9):1325-1335, 2015.

Janes, M.R. et al., Targeting KRAS mutant cancers with a covalent G12C-specific inhibitor. Cell, 172(3):578-589, 2018.

Kiel, C. et al.,. Im-proved binding of Raf to Ras.GDP is correlated with biological activity. Journal of Biological Chemistry, 284(46):31893-31902, 2009.

Kuhlman, B. et al., Native protein sequences are close to optimal for their structures. Proc Natl Acad Sci U S A, 97(19):10383-8, 2000.

Leach, A. R. et al. Exploring the conformational space of protein side chains using dead-end elimination and the A* algorithm. Proteins, 33(2):227-39, 1998.

Leaver-Fay, A. et al. Rosetta3: an object-oriented software suite for the simulation and design of macromolecules. Methods Enzymol, 487:545-74, 2011.

Lee, C. et al., Prediction of protein side-chain conformation by packing optimization. eng. Journal of Molecular Biology, 217(2):373-388, 1991. ISSN: 0022-2836.

Lee, J. New Monte Carlo algorithm: entropic sampling. Physical Review Letters, 71(2):211, 1993.

Lilien, R. H. et al., A novel ensemble-based scoring and search algorithm for protein redesign and its application to modify the substrate specificity of the gramicidin synthetase a phenylalanine adenylation enzyme. J Comput Biol, 12(6):740-61, 2005.

Lito, P. et al., Allele-specific inhibitors inactivate mutant KRAS G12C by a trapping mechanism. Science, 351(6273):604-608, 2016.

Lou, Q. et al. Dynamic importance sampling for anytime bounds of the partition function. In Advances in Neural Information Processing Systems, pp. 3196-3204, 2017.

Lovell, S. C. et al., The penultimate rotamer library. Proteins, 40(3):389-408, 2000.

Maurer, T. et al., Small-molecule ligands bind to a distinct pocket in Ras and inhibit sos-mediated nucleotide exchange activity. Proceedings of the National Academy of Sciences, 109(14):5299-5304, 2012.

Nassar, N. et al., Ras/Rap effector specificity determined by charge reversal. Nature Structural and Molecular Biology, 3(8):723, 1996.

Nose, S. A molecular dynamics method for simulations in the canonical ensemble. Molecular physics, 52(2):255-268, 1984.

Ojewole, A. A. et al., BBK* (branch and bound over K*): a provable and efficient ensemble-based algorithm to optimize stability and binding affinity over large sequence spaces. In Springer International Publishing, 2017, pp. 157-172.

Ojewole, et al., OSPREY predicts resistance mutations using positive and negative computational protein design. In Computational Protein Design, part 15, pp. 291-306. Springer, 2017.

Ostrem, J. M. et al., K-Ras (G12C) inhibitors allosterically control GTP affinity and effector interactions. Nature, 503(7477):548, 2013.

Papke, B. et al. Drugging RAS: know the enemy. Science, 355(6330):1158-1163, 2017.

Patricelli, M. P. et al. Selective inhibition of oncogenic KRAS output with small molecules targeting the inactive state. Cancer discovery, 6(3):316-329, 2016.

Pearlman, D. Pearlman, et al., AMBER: a package of computer programs for applying molecular mechan-ics, normal mode analysis, molecular dynamics and free energy calculations to simulate the structural and energetic properties of molecules. Comput Phys Commun, 91(42):1-41, 1995.

Reeve, S. M. et al., Protein design algorithms predict viable resistance to an experimental antifolate. Proc Natl Acad Sci U S A, 112(3):749-54, 2015.

Roberts, K. E. et al., Computational design of a PDZ domain peptide inhibitor that rescues CFTR activity. PLoS Comput Biol, 8(4):e1002477, 2012.

Roberts, K. E. et al., Fast gap-free enumeration of conformations and sequences for protein design. Proteins, 83(10):1859-77, 2015.

Roberts, K. E. https://www2.cs.duke.edu/donaldlab/software/proteinInteractionViewer/ Protein Interaction Viewer, 2012.

Rudicell, R. S. et al. Enhanced potency of a broadly neutralizing HIV-1 antibody in vitro improves protection against lentiviral infection in vivo. J Virol, 88(21):12669-82, 2014.

Sciretti, D. et al., Computational protein design with side-chain conformational entropy. Proteins, 74(1):176-91, 2009.

Silver, N. W. et al., Efficient computation of small-molecule configurational binding entropy and free energy changes by ensemble enumeration. J Chem Theory Comput, 9(11):5098-5115, 2013.

Simoncini, D., et al., Guaranteed discrete energy optimization on large protein design problems. J Chem Theory Comput, 11(12):5980-9, 2015.

Sommer, R. et al., The virulence factor LecB varies in clinical isolates: consequences for ligand binding and drug discovery. Chemical Science, 7(8):4990-5001, 2016.

Stevens, B. W. et al., Redesigning the PheA domain of gramicidin synthetase leads to a new understanding of the enzyme's mechanism and selectivity. Biochemistry, 45(51):15495-504, 2006.

Sun, Q. et al., Discovery of small molecules that bind to K-Ras and inhibit Sos-mediated activation. Angewandte Chemie International Edition, 51(25):6140-6143, 2012.

Sydor, J. R. et al., Cell-free synthesis of the ras-binding domain of c-Raf-1: binding studies to fluorescently labelled H-Ras. FEBS letters, 452(3):375-378, 1999.

Traore, S. et al. A new framework for computational protein design through cost function network optimization. Bioinformatics, 29(17):2129-36, 2013.

Traore, S. et al., Deterministic search methods for computational protein design. Methods Mol Biol, 1529:107-123, 2017.

Traore, S. et al., Fast search algorithms for computational protein design. J Comput Chem, 37(12):1048-58, 2016.

Tzeng, S.-R. et al., Protein activity regulation by conformational entropy. Nature, 488(7410):236, 2012.

Viricel, C. et al., Guaranteed weighted counting for affinity computation: beyond determinism and structure. In International Conference on Principles and Practice of Constraint Programming, pp. 733-750. Springer, 2016.

Zeng, M. et al., Potent and selective covalent quinazoline inhibitors of KRAS G12C. Cell chemical biology, 24(8):1005-1016, 2017.

Fakih et al., Phase 1 study evaluating the safety, tolerability, pharmacokinetics (PK), and efficacy of AMG 510, a novel small molecule KRASG12C inhibitor, in advanced solid tumors. J Clin Onc, May 20, 2019, 37(15);3003. 2 pages.

Jou et al., Minimization-Aware Recursive K*: A Novel, Provable Algorithm that Accelerates Ensemble-Based Protein Design and Provably Approximates the Energy Landscape. J Comput Biol. Apr. 2020;27(4):550-564.

Lakshman et al., Quantitative biophysical analysis defines key components modulating recruitment of the GTPase KRAS to the plasma membrane. J Biol Chem. Feb. 8, 2019;294(6):2193-2207.

Lowegard, Apr. 26, 2017: Computational Design of Peptide Inhibitors of KRAs Protein-Protein interactions. Seminar, Swedish University of Agricultural Sciences, Uppsala, Sweden. 51 pages.

Lowegard, Apr. 26, 2017: Computational Design of Peptide Inhibitors of KRAs Protein-Protein interactions. Seminar, University of Uppsala, Uppsala, Sweden. 51 pages.

Lowegard, Oct. 2, 2018: Redesigning the KRas/c-Raf-RBD Protein-Protein Interface. Seminar, Science of Life Laboratory, Stockholm, Sweden. 38 pages.

Lowegard, Oct. 4, 2018: Redesigning the KRas/c-Raf-RBD Protein-Protein Interface. Seminar, Uppsala University, Uppsala, Sweden. 38 pages.

Lowegard. Novel Algorithms and Tools for Computational Protein Design with Applications to Drug Resistance Prediction, Antibody Design, Peptide Inhibitor Design, and Protein Stability Prediction. Dissertation, Graduate Program in Computational Biology and

(56) References Cited

PUBLICATIONS

Bioinformatics in the Graduate School of Duke University. Publicly Available May 21, 2021. 161 pages.

Lowegard. Novel Algorithms and Tools for Computational Protein Design with Applications to Drug Resistance Prediction, Antibody Design, Peptide Inhibitor Design, and Protein Stability Prediction. Dukespace, Scholarship by Duke Authors. 3 pages. Retrieved from the internet Apr. 19, 2024. Retrieved from <https://hdl.handle.net/10161/18807>.

Frenkel. Combined Computational, Experimental, and Assay-Development Studies of Protein: Protein and Protein: Small Molecule Complexes, with Applications to the Inhibition of Enzymes and Protein: Protein Interactions. Dissertation, Department of Biochemistry Duke University.Publicly Available Jan. 10, 2022. 235 pages.

Frenkel. Combined Computational, Experimental, and Assay-Development Studies of Protein: Protein and Protein: Small Molecule Complexes, with Applications to the Inhibition of Enzymes and Protein: Protein Interactions. Dukespace, Scholarship by Duke Authors. 3 pages. Retrieved from the internet Apr. 19, 2024. Retrieved from <https://hdl.handle.net/10161/20091>.

* cited by examiner

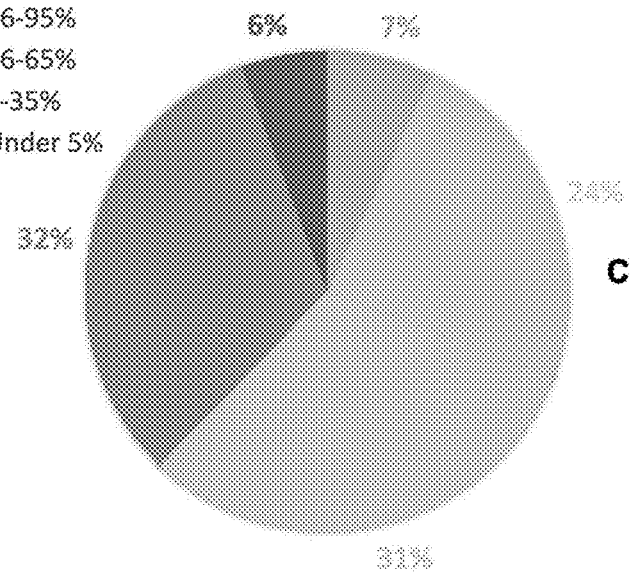
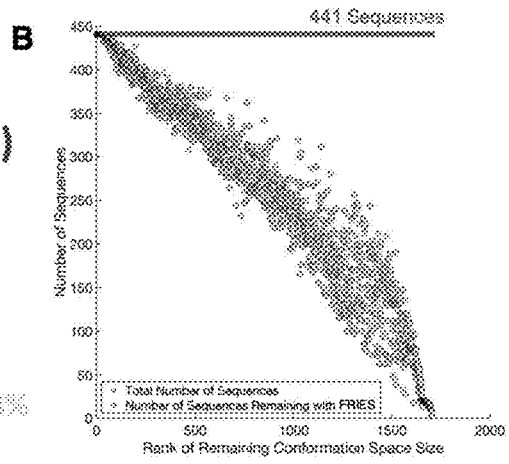
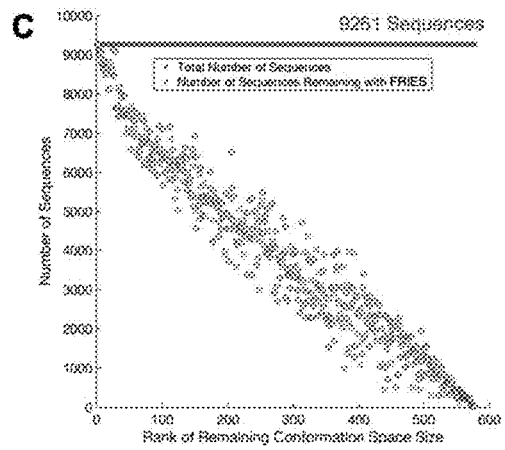
FIG. 3A-C

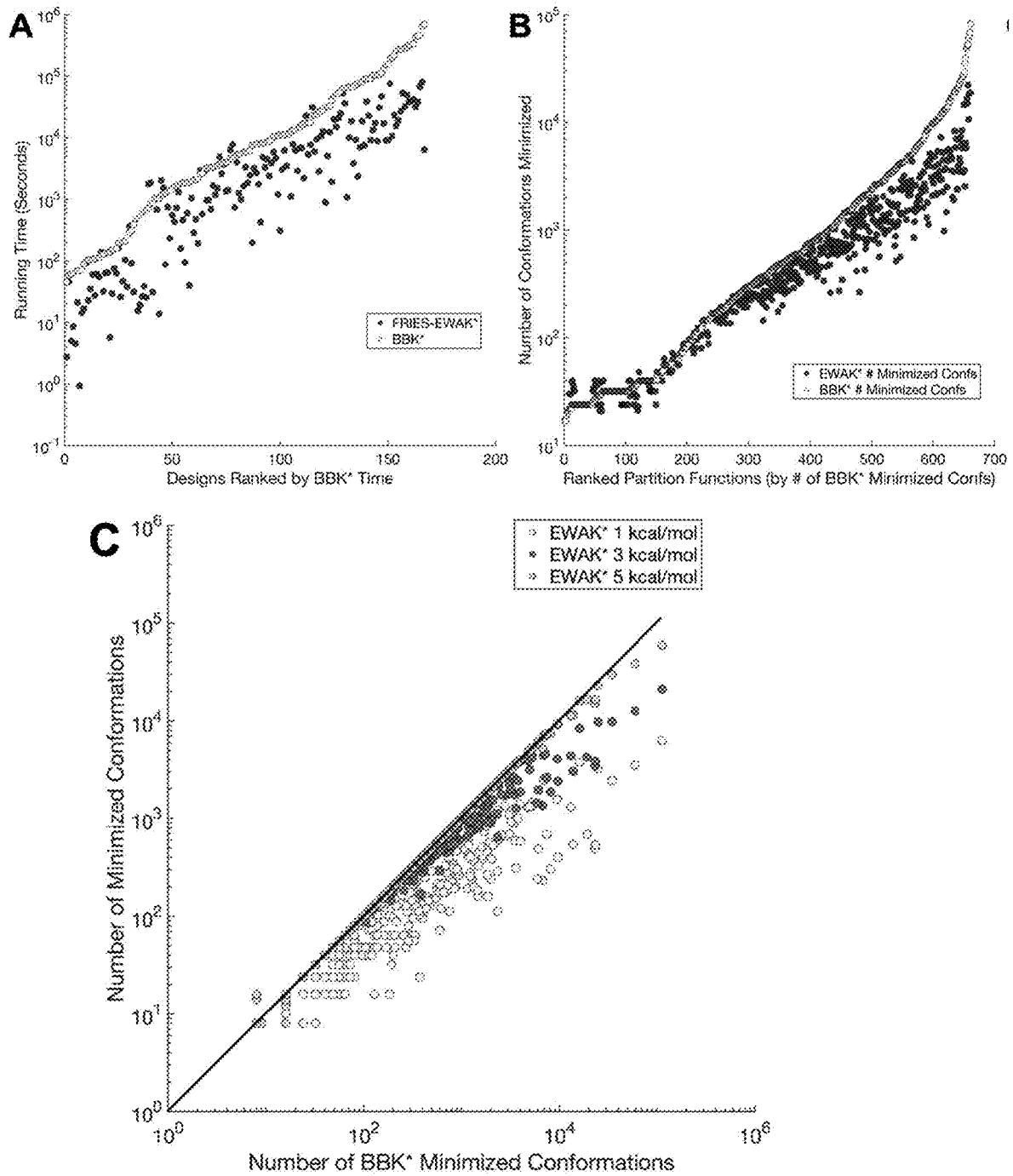
FIG. 4A-C

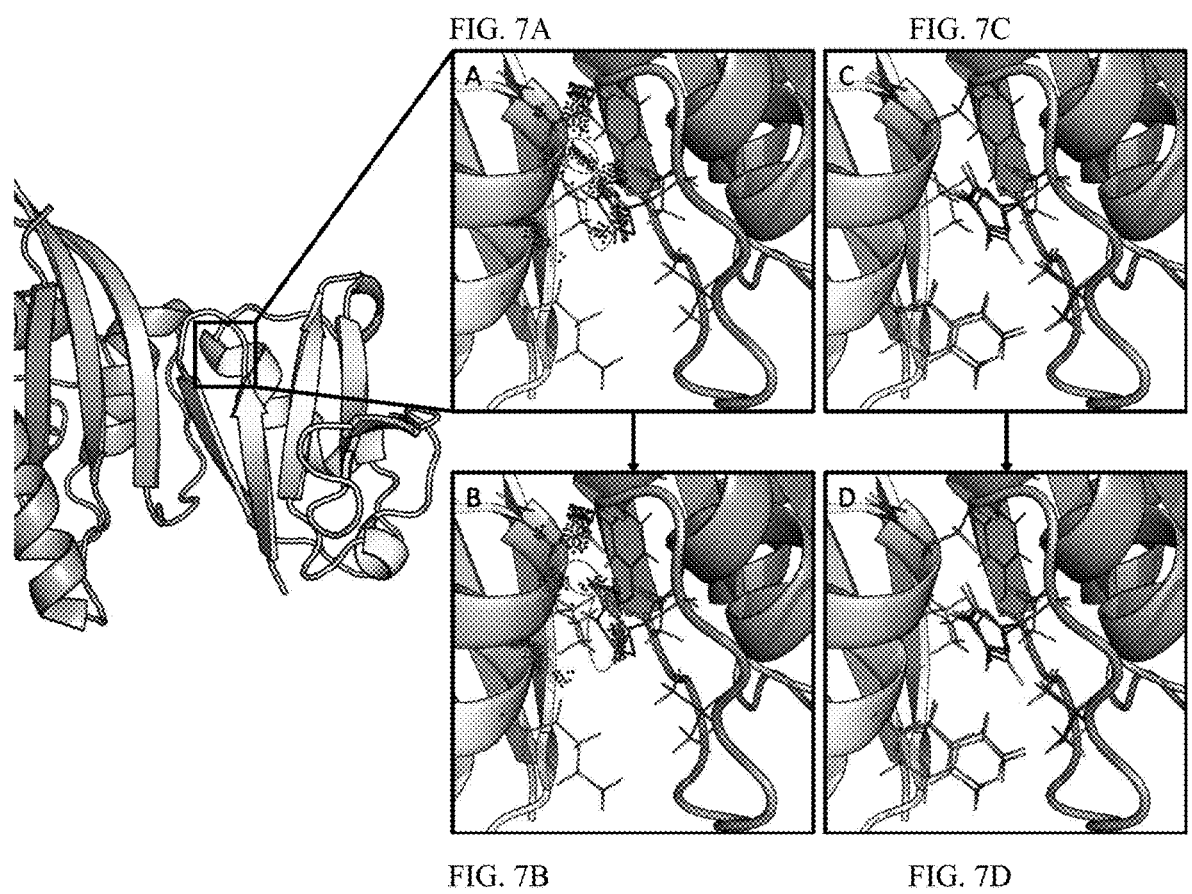

FIG. 8A  FIG. 8C  FIG. 8E
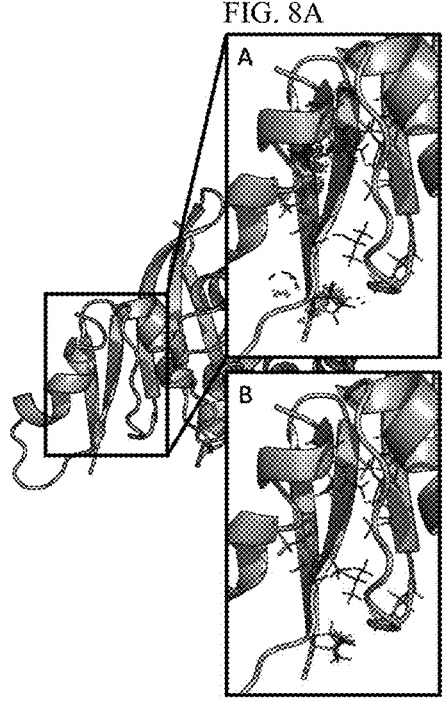
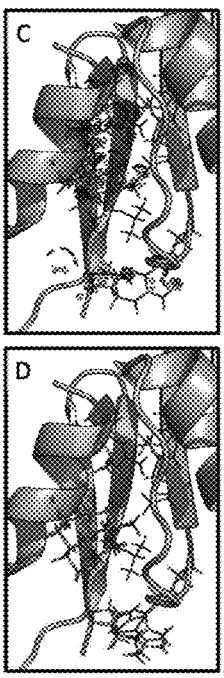
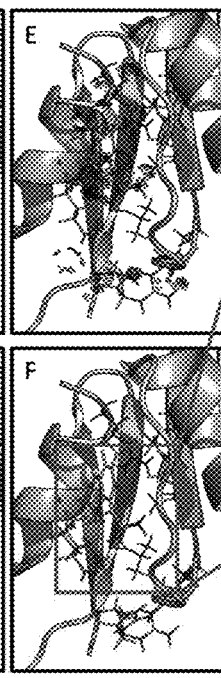
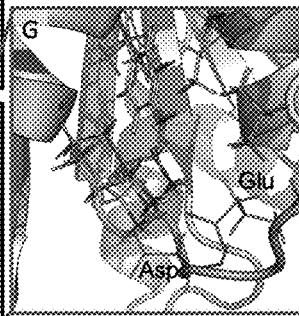
| c-Raf-RBD Variant | Lower Bound log ($K^*$) | Upper Bound log ($K^*$) |
|---|---|---|
| Wild-Type | 30.67 | 30.77 |
| c-Raf-RBD(RK) | 38.80 | 39.12 |
| c-Raf-RBD(RKY) | 39.29 | 39.80 |
FIG. 8B  FIG. 8D  FIG. 8F  FIG. 8G

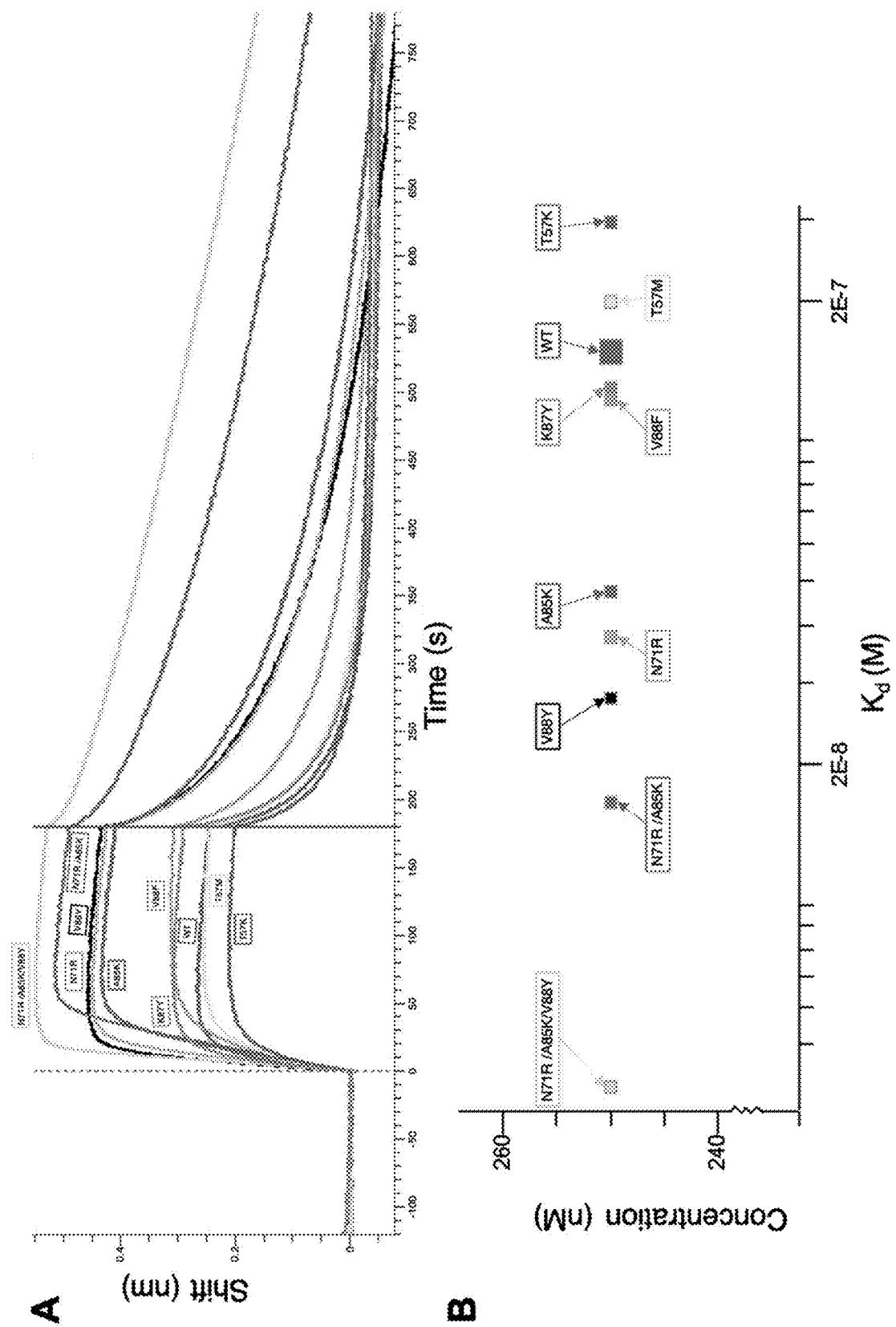
FIG. 9A-B

COMPOSITIONS FOR INHIBITING KRas SIGNALING AND METHODS OF MAKING AND USING SAME

STATEMENT REGARDING RELATED APPLICATIONS

This application claims priority to U.S. Provisional Patent Application No. 63/030,975, filed May 28, 2020, the entire contents of which are incorporated herein by reference for all purposes.

STATEMENT OF GOVERNMENT INTEREST

This invention was made with Government support under Federal Grant no. R01 GM078031 awarded by the National Institutes of Health. The Federal Government has certain rights to this invention.

BACKGROUND

Computational structure-based protein design (CSPD) is an innovative tool that enables the prediction of protein sequences with desired biochemical properties, such as improved binding affinity. OSPREY (Open Source Protein Redesign for You) is an open-source, state-of-the-art software package used for CSPD. OSPREY's algorithms focus on provably returning the optimal sequences and conformations for a given input model. In contrast, stochastic, non-deterministic approaches provide no guarantees on the quality of conformations, or sequences, and make determining sources of error in predicted designs very difficult.

OSPREY has been used successfully on several empirical, prospective designs including designing enzymes, resistance mutations, protein-protein interaction (PPI) inhibitors, epitope-specific antibody probes, and broadly-neutralizing antibodies. These successes have been validated experimentally in vitro and in vivo and are now being tested in several clinical trials. However, while OSPREY has been successful in the past, as the size of protein design problems grows (e.g., when considering a large protein-protein interface), enumerating and minimizing the necessary number of conformations and sequences to satisfy the provable halting criteria in previous K*-based algorithms becomes prohibitive (despite recent algorithmic improvements). The entire conformation space can be monumental in size and heavily populated with energetically unfavorable sequences and conformations. Accordingly, what is needed are improved methods for protein design with improved runtimes and minimized unfavorable input sequences.

SUMMARY

Computational structure-based protein design is an innovative tool for redesigning proteins to introduce a particular or novel function. One such function is improving the binding of one protein to another, which can increase understanding of biomedically important protein systems toward the improvement or development of novel therapeutics. Accordingly, one aspect of the present disclosure provides novel computational methods that comprise provable algorithms (termed FRIES and EWAK*) for more efficient computational structure-based protein design. In another aspect, provided herein is application of the method disclosed herein to the redesign of the c-Raf-RBD:KRas protein-protein interface. These new methods and incorporated algorithms speed-up computational structure-based protein design while maintaining accurate calculations, allowing for larger, previously infeasible protein designs.

In some aspects, provided herein are computational methods for protein design. In some embodiments, the computational method for protein design comprises providing a set of input sequences. The set of input sequences comprises a wild-type protein sequence, a plurality of variant protein sequences, a wild-type ligand sequence, and a plurality of variant ligand sequences. The method further comprises using a computer to apply an algorithm to the set of input sequences, wherein the algorithm independently performs multiple tasks to prune the set of input sequences (e.g. to remove variant sequences having undesirable characteristics.). For example, in some embodiments the algorithm removes variant protein sequences having a partition function value at least m orders of magnitude away from a partition function value for the wild-type protein sequence in an unbound state. In some embodiments, the algorithm removes variant ligand sequences having a partition function value at least m orders of magnitude away from a partition function value for the wild-type ligand sequence in an unbound state. In some embodiments, the algorithm removes one or more sequences in a variant complex having a partition function value at least m orders of magnitude away from a partition function value for a wild-type complex containing the wild-type protein bound to the wild-type ligand. The variant complex comprises a variant protein sequence and/or a variant ligand sequence, either or both of which may be removed. For all of the above steps, m is a user defined value. The computer-implemented method generates a set of output sequences which contains fewer total sequences than the set of input sequences.

In some embodiments, the algorithm removes variant protein sequences having an upper bound on the partition function value at least m orders of magnitude away from a lower bound on the partition function value for the wild-type protein sequence in an unbound state. In some embodiments, the algorithm removes variant ligand sequences having an upper bound on the partition function value at least m orders of magnitude away from a lower bound on the partition function value for the wild-type ligand sequence in an unbound state. In some embodiments, the algorithm removes one or more sequences in a variant complex having an upper bound on the partition function value at least m orders of magnitude away from a lower bound on the partition function value for a complex containing the wild-type protein bound to the wild-type ligand.

In some embodiments, the algorithm is further configured to enumerate input sequences in order of increasing lower bound on minimized energy. For example, in some embodiments the algorithm is configured to enumerate input sequences in order of increasing lower bound on minimized energy and identify the wild-type protein sequence and the wild-type ligand sequence based upon the lower bounds on minimized energy. The algorithm may be further configured to calculate a minimized energy of the wild-type protein sequence and the wild-type ligand sequence in a given conformation. The algorithm may be further configured to calculate a minimized energy of a wild-type complex (e.g. a complex comprising the wild-type protein sequence bound to the wild-type ligand sequence).

In some embodiments, the algorithm is configured to remove variant protein sequences having a lower bound of minimized energy greater than the sum of the minimized energy of the wild-type protein sequence in the given conformation and an energy window value w. In some embodiments, the algorithm is configured to remove variant ligand sequences having a lower bound of minimized energy greater than the sum of the minimized energy of the wild-type ligand sequence in the given conformation and an energy window value w. In some embodiments, the algorithm is configured to remove one or more sequences in a variant complex having a lower bound of minimized energy greater than the sum of the minimized energy of the wild-type complex and an energy window value w. The complex comprises a variant protein sequence and/or a variant ligand sequence. For all of the above steps, w is user defined. In this manner, the algorithm generates a subset of pruned sequences, which may be used as the set of input sequences provided to the algorithm to eliminate sequences based upon partition function value.

In some embodiments, the algorithm is further configured to calculate a lower bound of a partition function value for the wild-type protein sequence in an unbound state, the wild-type ligand sequence in an unbound state, and the wild-type complex. In some embodiments, calculating the lower bound of the partition function value for the wild-type protein sequence in an unbound state comprises Boltzmann-weighting the minimized energy of the wild-type protein sequence in the given conformation. In some embodiments, calculating the lower bound of the partition function value for the wild-type ligand sequence in the unbound state comprises Boltzmann-weighting the minimized energy of the wild-type ligand sequence in the given conformation. In some embodiments, calculating the lower bound of the partition function value for the wild-type complex comprises Boltzmann-weighting the minimized energy of the wild-type complex.

In some embodiments, the algorithm is further configured to calculate an upper bound of a partition function value for each variant protein sequence in an unbound state, for each variant ligand sequence in an unbound state, and for each variant complex. In some embodiments, calculating the upper bound of the partition function value for each variant protein sequence comprises Boltzmann-weighting the lower bound of minimized energy for the variant sequence and multiplying by the size of the conformation space for the variant protein sequence. In some embodiments, calculating the upper bound of the partition function value for each variant ligand sequence comprises Boltzmann-weighting the lower bound of minimized energy for the ligand sequence and multiplying by the size of the conformation space for the variant protein sequence. In some embodiments, calculating the upper bound of the partition function value for each variant complex comprises Boltzmann-weighting the lower bound of minimized energy for the variant complex and multiplying by the size of the conformation space for the variant complex.

The methods described herein result in generation of a set of output sequences. The set of output sequences comprises a wild-type protein sequence, a plurality of variant protein sequences, a wild-type ligand sequence, and a plurality of variant ligand sequences. The set of output sequences comprises fewer total sequences than the set of input sequences. For example, the set of output sequences may comprise at least 5% fewer total sequences than the set of input sequences. In some embodiments, the set of output sequences comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% fewer total sequences than the set of input sequences.

In some embodiments, the methods further comprise predicting a binding affinity of at least one variant sequence in the set of output sequences. For example, predicting a binding affinity may comprise predicting the affinity of a variant ligand sequence for a protein sequence (e.g. a variant protein sequence or a wild-type protein sequence). As another example, predicting a binding affinity nay comprise predicting the affinity of a variant protein sequence for a wild-type ligand sequence. Predicting the binding affinity comprises assigning a K* score to the at least one variant sequence.

In another aspect, provided herein is a RAF proto-oncogene serine/threonine-protein kinase (c-RAF) mutant protein. In some embodiments, the protein comprises one or more mutations in a receptor binding domain (RBD) of the protein. For example, the one or more mutations may comprise T57M, T57K, K87Y, V88Y, V88F, or a combination thereof. In some embodiments, the protein comprises a V88Y substitution mutation. In some embodiments, the protein comprises a V88Y substitution mutation and at least one additional mutation. For example, the protein may comprise a V88Y substitution mutation and at least one additional mutation selected from the mutations listed in Table 4 herein. In some embodiments, the mutant protein comprises V88Y, N71R, and A85K substitution mutations.

In another aspect, provided herein is a polynucleotide encoding a c-RAF mutant protein described herein. In yet another aspect, provided herein is a cell expressing the polynucleotide encoding the c-RAF mutant protein.

In some aspects, provided herein are conjugates. The conjugates comprise a c-RAF mutant protein and another moiety. For example, in some embodiments the conjugate comprises a c-RAF mutant protein and another moiety selected from a cell targeting moiety, a cell penetrating moiety, or a combination thereof.

In another aspect, provided herein are methods of treating cancer in a subject. The methods comprise providing to the subject a conjugate comprising a c-RAF mutant protein as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A-C shows reduction in input sequence space size using FRIES in accordance with one embodiment of the present disclosure. (A) A pie chart representing the reduction in the sequence space in percentages across all 2,662 designs. 7% of the designs had a reduction in sequence space over 95%, 24% of the designs had a reduction in sequence space between 66-95%, 31% of the designs had a reduction in sequence space between 36-65%, 32% of the designs had a reduction in sequence space between 6-35%, and 6% of the designs had a reduction in sequence space under 5%. (B) and (C) plot the number of sequences remaining after using FRIES starting with 441 and 9,261 sequences total, respectively. The number of sequences remaining for each design are sorted in order of decreasing size of the remaining conformation space after FRIES.

FIG. 4A-C shows a comparison of runtimes and the number of minimized conformations between FRIES/EWAK* and BBK* for a variety of designs in accordance with one embodiment of the present disclosure. (A) A plot of the runtime in seconds (the y-axis is on a log scale) for FRIES/EWAK* and BBK* for 167 design examples. Each point represents one design and is plotted in increasing order of BBK running time. FRIES/EWAK* was faster than BBK*92% of the time with an average improvement of 62% over BBK* and a maximum improvement of 2.2 orders of magnitude. This improvement was evident in (A) since the FRIES/EWAK* times fall mostly below the BBK* times. (B) A plot of the number of conformations minimized (y-axis is on a log scale) for 661 partition function calculations from 161 design examples. The number of conformations minimized by EWAK* was less than the number of conformations minimized by BBK* in 68% of these cases, as is evidenced by the EWAK* dots landing mostly below the BBK* dots. In the best case, EWAK* decreased the number of conformations by 1.1 orders of magnitude. The average percent reduction in the number of minimized conformations was 27%. (C) Each dot represents a calculated partition function. The different color dots indicate partition functions limited to within a 1.0 kcal/mol window of the GMEC, partition functions limited to a 3.0 kcal/mol window of the GMEC, and partition functions limited to within a 5.0 kcal/mol window of the GMEC, respectively. These dots are plotted according to the number of minimized conformations required for each corresponding BBK* partition function calculation. The solid black line represents the number of BBK* minimized conformations, so dots that fall below the black line represent examples that required fewer minimized conformations than with BBK*. As they approach the 5.0 kcal/mol window, the dots begin to converge with the BBK* line. However, as the number of BBK* minimized conformations rises beyond 104, even the dots corresponding to partition functions limited to within a 5.0 kcal/mol window of time of the GMEC drop below the BBK* line.

FIG. 7A-D shows the redesign of c-Raf-RBD residue position 88 from valine to isoleucine in accordance with one embodiment of the present disclosure. The left-hand side shows c-Raf-RBD in complex with KRas. Panels (A-D) zoom in on one particular design at residue position 88 and are rotated 180°. Residue position 88 has a valine in the native, wild-type sequence (panels A & C) which was redesigned to an isoleucine (panels B & D). A mutation to isoleucine at this position was computationally predicted by EWAK* to decrease the binding of c-Raf-RBD to KRas$^{GTP}$. This was experimentally validated in [48], where the authors incorrectly computationally predicted the affect of this particular mutation on the binding of c-Raf-RBD to KRas$^{GTP}$. (A) The wild-type residue (valine) is shown with dots that indicate molecular interactions [66] with the surrounding residues (residues allowed to be flexible in the design are shown as lines). (B) The mutant residue (isoleucine) is shown with dots that indicate molecular interactions [66] with the surrounding residues (residues allowed to be flexible in the design are shown as lines). Contacts made by the wild-type valine residue (circled dots in (A)) were lost upon mutation to isoleucine (circled space in (B)). (C & D) A set of 10 low-energy conformations that were included in the corresponding partition function calculation are shown for the wild-type (C) and the variant (D).

FIG. 8A-H shows the computational predictions in the protein-protein interface of the c-Raf-RBD:KRas complex for c-Raf-RBD(RK) and the novel variant c-Raf-RBD (RKY) in accordance with one embodiment of the present disclosure. Shown on the left is only the relevant protein-protein interface between c-Raf-RBD and KRas. Each panel zooms in on this interface and details a different c-Raf-RBD variant and its corresponding computational predictions. The upper and lower bounds on the log(K*) score for each design variant (wild-type, c-Raf-RBD(RK), and c-Raf-RBD (RKY)) are given in the bottom table (FIG. 8H). These computational predictions correspond with and are supported by the experimental results presented herein. Panels (A) and (B) show the wild-type sequence, panels (C) and (D) show the variant c-Raf-RBD(RK), and panels (E) and (F) show the novel computationally predicted variant c-Raf-RBD(RKY). Panels (A), (C), and (E) show the wild-type, c-Raf-RBD(RK), and c-Raf-RBD(RKY), respectively, along with probe dots [66] that represent the molecular interactions within each structure calculated by OSPREY. These probe dots were selected to only show interactions between the residues included in the computational designs (shown as lines) with their surrounding residues. Panels (B), (D), and (F) show 10 low-energy structures from each conformational ensemble calculated by OSPREY/EWAK*. Panel (G) shows a zoomed-in overlay of the wild-type variant with the c-Raf-RBD variant that includes only the V88Y mutation. Arrows indicate the change in positioning of the lysine at residue position 84 upon mutation of residue position 88 from valine to tyrosine. When valine is present at position 88, the lysine residue primarily hydrogen bonds with an aspartate (labeled) in KRas. When valine is mutated to tyrosine (shown in cyan), the lysine at position 84 moves to make room for the tyrosine and positions itself to hydrogen bond with both the aspartate and the glutamate (labeled) in KRas.

FIG. 9A-B shows the single-concentration experimental screening of c-Raf-RBD variants binding to KRas using BLI in accordance with one embodiment of the present disclosure. (A) Binding curves are shown for each variant (labeled on the plot) tested at a concentration of 250 nM. The colors and labels in panel (A) correspond to those in panel (B). (B) Plot of estimated $K_d$ values for each tested variant from a single-concentration screen (plotted in panel (A)). The c-Raf-RBD(RKY) variant (on the far left) is a novel, newly discovered variant of c-Raf-RBD. Top variants were further validated and had their $K_d$ values calculated using BLI titration experiments (see FIG. 10).

DETAILED DESCRIPTION

Figure 1:
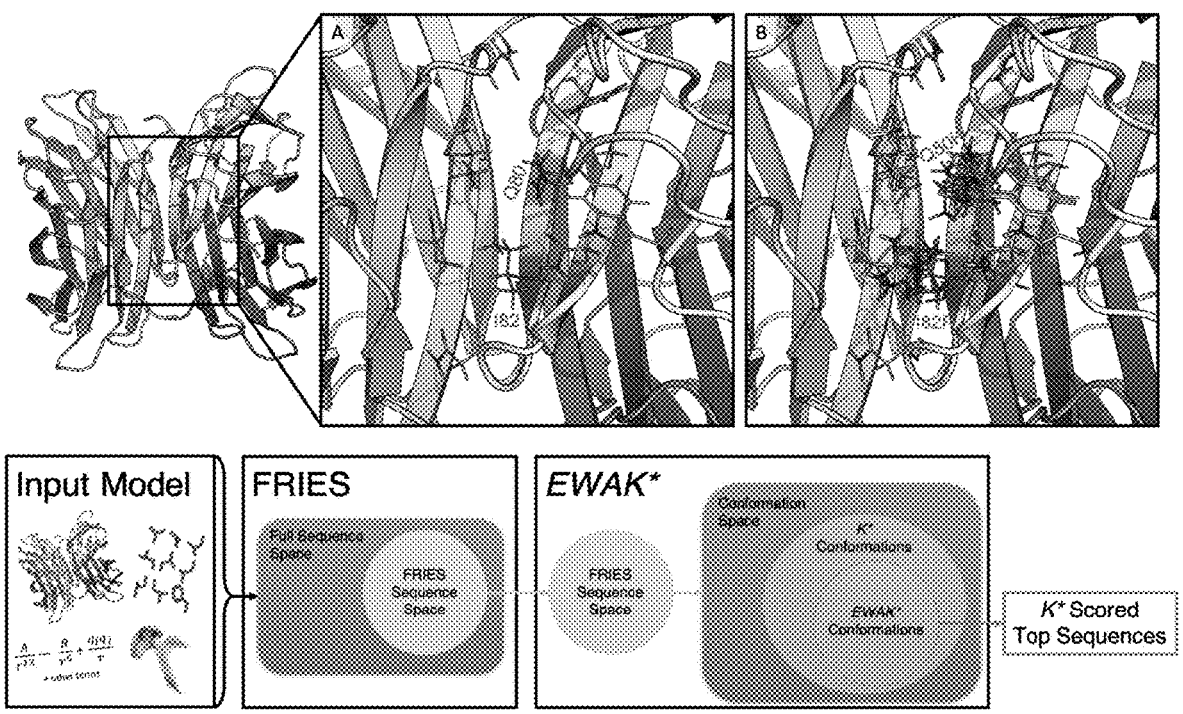
FIG. 1 shows a design example using the structure of the LecB lectin *Pseudomonas aeruginosa* strain PA14 (PDB ID: 5A6Y) and the OSPREY workflow for FRIES/EWAK* in accordance with one embodiment of the present disclosure. In the top panel, the full, 4 domain structure of lectin is shown on the left-hand side. (A) Zooming in on the region where domains A and D interact, showing the two mutable residues (Q80 and I82) along with the surrounding flexible shell of residues as lines. There were 11 flexible residues included in this design with Q80 and I82 allowed to mutate to all other amino acids except for proline. This design consisted of 8.102 $10^{11}$ conformations and 441 sequences. FRIES limited this space to 5.704 $10^{11}$ conformations and 206 sequences. FRIES/EWAK* in combination reduced the amount of time taken by about 75% compared to BBK*. FRIES alone was responsible for roughly 50% of this speed-up. (B) 10 low-energy conformations included in the thermodynamic ensemble of the design sequence with mutations Q80I and 182F. For this particular sequence, BBK minimized 10,664 conformations while EWAK* minimized only 4,104 conformations. The bottom panel shows the general workflow for FRIES/EWAK*. The workflow begins with the input model, which defines the design space for the first algorithm, FRIES. FRIES proceeds to prune the sequence space as illustrated in the Venn diagram with the unpruned space shown as a disk. Next, the remaining FRIES sequence space defines the conformation space (which contains multiple sequences as well as conformations) searched with EWAK*. EWAK* limits the conformations included in each partition function. EWAK* generally searches over only a subset of the conformations that previous K*-based algorithms like BBK*[32] search. EWAK* then returns the top sequences based on decreasing K* score.
Figure 2:
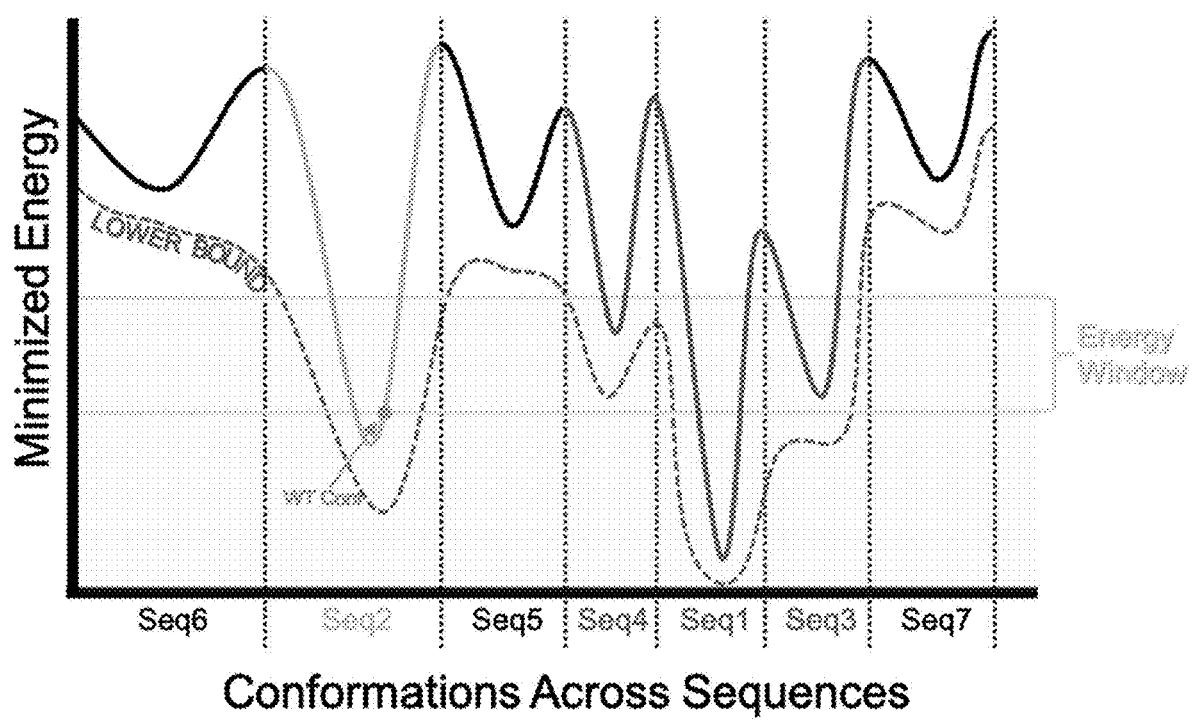
FIG. 2 shows how FRIES chooses which sequences to keep and which sequences to prune in accordance with one embodiment of the present disclosure. The solid curve represents the energy landscape of the conformation space that spans across, in this example, 7 different sequences (separated by dotted lines). Each sequence is labeled on the x-axis with an index indicating the order with which it is (or would be) enumerated with FRIES in order of increasing lower bound on minimized energy (dotted curve). FRIES continues to enumerate in this way until it encounters the wild-type sequence, at which point FRIES calculates the minimized energy $E_{WT}$ of the conformation with the lowest lower bound on minimized energy for the wild-type sequence (marked with a dot). $E_{WT}$ then becomes the baseline from which FRIES can provably enumerate all remaining sequences within some user-specified energy window w. Finally, FRIES prunes the sequences with energies provably higher than $E_{WT}$+w (black) and keeps the sequences that occur within the shaded region. More sequences are also pruned according to their partition function values as described in Eq (4).

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

1. Definitions

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The term "carrier" as used herein refers to any pharmaceutically acceptable solvent of agents that will allow a therapeutic composition to be administered to the subject. A "carrier" as used herein, therefore, refers to such solvent as, but not limited to, water, saline, physiological saline, oil-water emulsions, gels, or any other solvent or combination of solvents and compounds known to one of skill in the art that is pharmaceutically and physiologically acceptable to the recipient human or animal. The term "pharmaceutically acceptable" as used herein refers to a compound or composition that will not impair the physiology of the recipient human or animal to the extent that the viability of the recipient is compromised. For example, "pharmaceutically acceptable" may refer to a compound or composition that does not substantially produce adverse reactions, e.g., toxic, allergic, or immunological reactions, when administered to a subject.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

The terms "disease" and "disorder" as used herein include, but are not limited to, any abnormal condition and/or disorder of a structure or a function that affects a part of an organism. It may be caused by an external factor, such as an infectious disease, or by internal dysfunctions, such as cancer, cancer metastasis, and the like.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e. living organism, such as a patient).

Unless otherwise defined, all technical terms used herein have the same meaning as commonly understood by one of ordinary skill in the art to which this disclosure belongs.

2. Computational Methods

Computational structure-based protein design is an innovative tool for redesigning proteins to introduce a particular or novel function. One such function is improving the binding of one protein to another, which can increase understanding of biomedically important protein systems toward the improvement or development of novel therapeutics. In some aspects, provided herein are computational methods for protein design. In some embodiments, provided herein are computational methods for structure-based protein design.

The methods described herein may be used to optimize protein-protein interfaces (PPI). For example, the methods described herein may be used in optimizing interaction of two or more members in a protein complex. A protein consists of one or more polypeptide chains. Accordingly, a protein complex is a group of two or more associated polypeptide chains. Different polypeptide chains may have different functions. Protein complexes are a form of quaternary structure. Proteins in a protein complex are linked by non-covalent protein-protein interactions, and different protein complexes have different degrees of stability over time. These complexes are a cornerstone of many (if not most) biological processes and together they form various types of molecular machinery that perform a vast array of biological functions.

A computer (or database) representation of a protein complex comprises the sequence of each of the component proteins in the complex, together with a structural and dynamic characterization of the three-dimensional shape of each polypeptide chain, which can be determined or predicted using a variety of experimental or computational techniques. For example, a PDB file Contains the 3 dimensional coordinates and bond connectivity for all atoms in the protein complex together with sequence information defining the amino acid composition of each of the several polypeptide chains. Thus, a computer (or data) model of a protein complex may be specified by listing the amino acid sequence of each of the several component polypeptide chains, together with a statement that these chains bind together in a complex in vitro or in vivo. Information on the disulfide cross-linking, post translational modifications, and three-dimensional structure of the atoms of the several polypeptides, in absolute coordinates and also in relation to one another reflecting the empirical spatial arrangement of the complex as a physical object, are determined, predicted, or provided to facilitate mechanistic studies and structure-based drug/inhibitor/protein design.

In some embodiments, the methods described herein may be used to predict the sequences of variant polypeptide chains that will form complexes with desired properties (such as enhanced affinity, specificity activity), predict the 3D structures that the variants will assume in vitro together, and to predict binding affinity of variant polypeptide chains for the target (e.g. for a binding partner)

In some embodiments, the computational method for protein design comprises providing a set of input sequences. The set of input sequences comprises a wild-type protein sequence. The wild-type protein sequence may be for any protein of interest. In some embodiments, the wild-type protein is a receptor, and the wild-type protein sequence is the sequence for that receptor. The set of input sequences further comprises a plurality of variant protein sequences. For example, the set of input sequences may further comprise a plurality of variant receptor sequences. The set of input sequences further comprises a wild-type ligand sequences. For example, the set of input sequences may comprise a wild-type receptor sequence and a wild-type ligand sequence, wherein the wild-type ligand is known to or suspected of binding to the wild-type receptor. The set of input sequences further comprises a plurality of variant ligand sequences.

The method further comprises using a computer to apply an algorithm to the set of input sequences. The algorithm performs multiple tasks to facilitate generation of a set of output sequences. The set of output sequences comprises fewer total sequences than the set of input sequences. The process of removing input sequences to arrive at the set of output sequences is referred to herein as "pruning" or "sequence pruning". In some embodiments, multiple pruning steps occur in the process prior to arriving at the final set of output sequences. The method described herein involving pruning input sequences to arrive at a set of output sequences is referred to herein as Fast Removal of Inadequately Energised Sequences, or "FRIES".

The set of output sequences may subsequently be used in an algorithm that selects optimal variant sequences, such as optimal variant ligand sequences with high binding affinity for a receptor (e.g. high affinity for a protein sequence). The method for predicting binding affinity for the set of output sequences (e.g. the set of output sequences obtained using FRIES) is referred to herein as Energy Window Approximation to K* (EWAK*). The combination of FRIES/EWAK* is a powerful tool for computational structure-based protein design.

In some embodiments, the algorithm is configured to remove variant sequences. In some embodiments, the algorithm removes variant protein sequences, variant ligand sequences, and/or one or more sequences present in a variant complex. In some embodiments, the algorithm removes variant protein sequences, variant ligand sequences, and one or more sequences present in a variant complex. As used herein, the term "wild-type complex" refers to a complex containing the wild-type protein (e.g. receptor) bound to the wild-type ligand. In contrast, the term "variant complex" refers to a complex containing a variant protein sequence and/or a variant ligand sequence. For example, a variant complex may contain a wild-type protein bound to a variant ligand. Alternatively, a variant complex may contain a variant protein bound to a wild-type ligand. Alternatively, a variant complex may contain a variant protein bound to a variant ligand.

In some embodiments, the algorithm is configured to enumerate input sequences in order of increasing lower bound on minimized energy. For example, the algorithm may be configured to enumerate input protein sequences and input ligand sequences in order of increasing lower bound on minimized energy. In some embodiments, the algorithm is configured to identify the wild-type protein sequence and the wild-type ligand sequence based upon the lower bounds on minimized energy.

In some embodiments, the algorithm is further configured to calculate a minimized energy for the wild-type protein sequence in a given conformation, the wild-type ligand sequence in a given conformation, and/or the wild-type complex. For example, in some embodiments the algorithm is further configured to calculate the minimized energy of the wild-type protein sequence in a given unbound conformation. The algorithm may additionally be configured to calculate the minimized energy of the wild-type ligand sequence in a given unbound conformation. The algorithm may additionally be configured to calculate the minimized energy of the wild-type complex.

In some embodiments, the algorithm is configured to remove variant sequences based upon the lower bound of minimized energy of the sequences. In some embodiments, the algorithm is configured to remove variant sequences having a lower bound of minimized energy greater than the sum of the minimized energy of the wild-type sequence in the given conformation and an energy window value w, wherein w is user defined. For example, the algorithm may be configured to remove variant protein sequences having a lower bound of minimized energy greater than the sum of the minimized energy of the wild-type protein sequence in the given conformation (e.g. an unbound conformation) and an energy window value w, wherein w is user defined. The algorithm may additionally be configured to remove variant ligand sequences having a lower bound of minimized energy greater than the sum of the minimized energy of the wild-type ligand sequence in the given conformation (e.g. an unbound conformation) and an energy window value w, wherein w is user defined. The algorithm may additionally be configured to remove one or more sequences in a variant complex having a lower bound of minimized energy greater than the sum of the minimized energy of the wild-type complex.

Accordingly, in some embodiments any variant sequence (including variant protein sequences and variant ligand sequences) with a lower bound on minimized energy not satisfying the following criterion is pruned:

$$E_v^e \leq E_{WT} + w. \quad \text{(equation 3)}$$

Wherein $E_v^e$ is the lower bound on minimized energy for the variant sequence, $E_{WT}$ is the minimized energy of the wild-type sequence, and w is the user defined window. The user defined window w may be the same or different value depending on whether the algorithm is applied to variant protein sequences, variant ligand sequences, or variant complexes.

Removal of these variant sequences based upon the lower bound of minimized energy of the sequence may generate a subset of pruned sequences. The subset of pruned sequences contains less sequences than the initial set of input sequences initially applied to the algorithm.

In some embodiments, the algorithm is further configured to calculate a lower bound of a partition function value for the wild-type protein sequence, the wild-type ligand sequence, and/or the wild-type complex. The lower bound of the partition function value may be calculated for the wild-type protein sequence and the wild-type ligand sequence in an unbound state. Calculating the lower bound of the partition function value comprises Boltzmann-weighting the minimized energy of the wild-type sequence in the given conformation. Boltzmann-weighting the minimized energy of the wild-type sequence is shown in Equation 5, below, where $E_{WT}$ is the minimized energy of the wild-type sequence, R is the gas constant, and T is the temperature.

$$q_{WT}^e = \exp(-E_{WT}/RT). \quad \text{(equation 5)}$$

For example, calculating the lower bound on the partition function value for the wild-type protein sequence in an unbound state comprises Boltzmann-weighting the minimized energy of the wild-type protein sequence in the unbound conformation. As another example, calculating the lower bound of the partition function value for the wild-type ligand sequence in the unbound state comprises Boltzmann-weighting the minimized energy of the wild-type ligand sequence in the unbound state. In some embodiments, calculating the lower bound of the partition function value for the wild-type complex comprises Boltzmann-weighting the minimized energy of the wild-type complex.

In some embodiments, the algorithm is further configured to calculate an upper bound of a partition function value for each variant sequence. In some embodiments, the upper bound of the partition function value is calculated for each variant sequence remaining in the subset of pruned sequences (e.g. the subset of pruned sequences following removal of sequences not satisfying equation 3). In some embodiments, the algorithm may be configured to calculate an upper bound of a partition function value for each variant protein sequence in an unbound state. The algorithm may be further configured to calculate an upper bound of a partition function value for each variant ligand sequence in an unbound state. The algorithm may be further configured to calculate an upper bound of a partition function value for each variant complex.

Calculating the upper bound of the partition function value may comprise Boltzmann-weighting the lower bound of minimized energy for the variant sequence and multiplying by the size of the conformation space for the variant sequence. The upper bound $q_v^\oplus$ on the partition function for each sequence v may be calculated by Boltzmann-weighting the lower bound on its energy $E_v^e$ and multiplying it by the size of the conformation space for that particular sequence $|Q(v)|$ as shown in equation 4:

$$q_v^\oplus = |Q(v)|\exp(-E_v^e/RT). \quad \text{(equation 4)}$$

Calculating the upper bound on the partition function value for each variant protein sequence comprises Boltzmann-weighting the lower bound of minimized energy for the variant sequence and multiplying by the size of the conformation space for the variant protein sequence. Calculating the upper bound of the partition function value for each variant ligand sequence comprises Boltzmann-weighting the lower bound of minimized energy for the ligand sequence and multiplying by the size of the conformation space for the variant protein sequence. Calculating the upper bound of the partition function value for each variant complex comprises Boltzmann-weighting the lower bound of minimized energy for the variant sequence and multiplying by the size of the conformation space for the variant complex.

In some embodiments, the algorithm is configured to subsequently prune variant sequences having a partition function value at least m orders of magnitude away from a partition function value for the wildtype sequence. For example, in some embodiments the algorithm is configured to prune variant protein (e.g. variant receptor) sequences having a partition function value at least m orders of magnitude away from a partition function value for the wild-type protein sequence in an unbound state. The sequences may be the sequences in the subset of pruned sequences (e.g. the subset of pruned sequences not satisfying equation 3). In some embodiments, the algorithm removes variant ligand sequences having a partition function value at least m orders of magnitude away from a partition function value for the wild-type ligand sequence in an unbound state. In some embodiments, the algorithm removes one or more sequences in a variant complex having a partition function value at least m orders of magnitude away from a partition function value for a complex containing the wild-type protein bound to the wild-type ligand. For any and all of these steps, m is a user defined value. The value for m does not have to be the same for each step. In some embodiments, m is the same for each of the above removal steps. In some embodiments, m is a different value for one or more of the above removal steps.

In some embodiments, the algorithm independently performs each of the following:
  i. removes variant protein sequences having a partition function value at least m orders of magnitude away from a partition function value for the wild-type protein sequence in an unbound state, wherein m is a user defined value;
  ii. removes variant ligand sequences having a partition function value at least m orders of magnitude away from a partition function value for the wild-type ligand sequence in an unbound state, wherein m is a user defined value; and
  iii. removes one or more sequences in a variant complex having a partition function value at least m orders of magnitude away from a partition function value for a complex containing the wild-type protein bound to the wild-type ligand, wherein m is a user defined value.

In some embodiments, the algorithm removes variant sequences having an upper bound on the partition function value at least m orders of magnitude away from a lower bound on the partition function value for the wild-type sequence. For example, in some embodiments the algorithm removes variant protein sequences having an upper bound on the partition function value at least m orders of magnitude away from a lower bound on the partition function value for the wild-type protein sequence in an unbound state. In some embodiments, the algorithm removes variant ligand sequences having an upper bound on the partition function value at least m orders of magnitude away from a lower bound on the partition function value for the wild-type ligand sequence in an unbound state. In some embodiments, the algorithm removes one or more sequences in a variant complex having an upper bound on the partition function value at least m orders of magnitude away from a lower bound on the partition function value for the wild-type complex containing the wild-type protein bound to the wild-type ligand.

In some embodiments, the set of input sequences comprises at least 50 input sequences. For example, the set of input sequences may comprise at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000 input sequences, or more.

Removal of the variant sequences following any of the methods described above results in generation of a set of output sequences, which comprises fewer total sequences than the set of input sequences. In some embodiments, the set of output sequences comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% fewer total sequences than the set of input sequences. In some embodiments, the set of output sequences comprises a wild-type protein sequence, a plurality of variant protein sequences, a wild-type ligand sequence, and a plurality of variant ligand sequence.

In some embodiments, the method further comprises predicting the binding affinity of at least one variant sequence in the set of output sequences. For example, the method may further comprise predicting the binding affinity of at least one variant ligand sequence for a wild-type protein. As another example, the method may further comprise predicting the binding affinity of a wildtype ligand sequence for a variant protein sequence. As another example, the method may further comprise predicting the binding affinity of a variant ligand sequence for a variant protein sequence. Predicting the binding affinity thereby presents a means to select for variant ligand sequences and/or variant protein (e.g. receptor) sequences having optimal binding affinities to identify variants with improved binding compared to wild-type.

In some embodiments, predicting the binding affinity comprises assigning a K* score to the at least one variant sequence. The K* score is a ratio of the Boltzmann-weighted partition functions for a protein-ligand complex that estimates the association constant, Ka. Many protein design methods have focused on computing a global minimum energy conformation (GMEC). However, a protein in solution exists not as a single, low-energy structure, but as a thermodynamic ensemble of conformations. Models that only consider the GMEC may incorrectly predict biophysical properties such as binding because GMEC-based algorithms underestimate potentially significant entropic contributions. Accordingly, for the methods described herein assigning a K* score includes modeling thermodynamic ensembles. In some embodiments, assigning a K* score to the at least one variant sequence may comprise performing the K* algorithm, such as in OSPREY, using the set of output sequences generated by the pruning methods described above (i.e. FRIES) as input sequences for which thermodynamic ensembles are modeled.

In some embodiments, assigning a K* score to the at least one variant sequence may include performing the BBK* algorithm, which an improvement on the traditional K* algorithm that allows for multi-sequence design. Some algorithms design for binding affinity using ensembles are linear in the size of the sequence space N, where N is exponential in the number of simultaneously mutable residue positions. In contrast, BBK* is the first provable ensemble-based algorithm to run in time sublinear in N, making it possible not only to perform K* designs over large sequence spaces, but also to enumerate a gap-free list of sequences in order of decreasing K* score. In some embodiments, the method comprises modeling thermodynamic ensembles for the set of output sequences (e.g. the set of output sequences generated by the FRIES methods described above), and approximating the K* score for those ensembles within a user-specified energy window of the GMEC for each sequence.

In some embodiments, assigning a K* score may be performed by a method referred to herein as EWAK*, an Energy Window Approximation to K*, which restricts the conformations included in each sequence's thermodynamic ensemble. EWAK* guarantees that each conformational ensemble contains all of the lowest energy conformations within an energy window of the GMEC for each design sequence. The methods described above (FRIES) may provide a set of output sequences that is used for input sequences for EWAK*. The combination of these two methods mitigates this complexity problem by limiting the sequence space (e.g. the sequence space used to predict binding affinity) to only the most favorable, low energy sequences.

Previous algorithms have focused on optimizing for sequences whose conformations are similar in energy to that of the GMEC. In contrast, FRIES focuses on optimizing for sequences with energies better-than or comparable-to the wild-type sequence. FRIES guarantees that the restricted input sequence space includes all of the sequences within an energy window of the wild-type sequence, but excludes any potentially unstable sequences with significantly worse partition function values. Wild-type sequences are generally expected to be near-optimal for their corresponding folds. Therefore, limiting the sequence space to sequences energetically similar to or better than the wild-type sequence is reasonable. Compared to the previous state-of-the-art algorithm BBK*, FRIES and EWAK* improve runtimes by up to 2 orders of magnitude, FRIES decreases the size of the sequence space by up to more than 2 orders of magnitude, and EWAK* decreases the number of conformations included in partition function calculations by up to almost 2 orders of magnitude.

The methods described herein allow for optimization of one or both sides (e.g. both members) in a protein-protein interface. For example, the methods may allow optimization of both sides in a protein-protein interface, such as for selection of a variant ligand and a variant protein sequence that have optimal properties (e.g. optimal binding affinities, optimal specificities for the other, etc.). For example, the methods may be used to select for variant protein sequences and/or variant ligand sequences with improved properties compared to wild-type, such as improved binding affinity for a partner. In addition, the methods may be used to select for conformations of the protein and/or ligand that possess improved properties. Accordingly, the methods described herein represent a novel method for optimizing a protein-protein interface that permit optimization based upon conformation and/or sequence of one or both members (e.g. the ligand and/or the protein) of the interface.

3. KRas Inhibitors

The computational protein design methods described above were used to study the protein-protein interface (PPI) of KRasGTP in complex with its tightest-binding effector, c-Raf. KRas is an important cancer target that has historically been considered "undruggable". Deepening the understanding of the PPI between KRas and its effectors is an important step toward developing effective new therapeutics. For this study, the re-design of the c-Raf Ras-binding domain (c-Raf-RBD) in complex with KRasGTP(c-Raf-RBD:KRasGTP) was the focus.

The effect on binding of mutations in the c-Raf-RBD:KRasGTP protein protein interface was investigated. The effect of novel, previously unreported mutations in the PPI of the c-Raf-RBD:KRasGTPcomplex were also evaluated. The binding of top predicted c-Raf-RBD variants to KRas was then measured using a bio-layer interferometry (BLI) assay single-concentration screen. This screen suggested that one of the new computationally-predicted c-Raf-RBD variants c-Raf-RBD(Y), a c-Raf-RBD that includes the mutation V88Y—exhibits improved binding to KRasGTP. Next, a c-Raf-RBD variant, c-Raf-RBD(RKY), that included this new mutation, V88Y, together with two previously reported mutations, N71R and A85K, was created. The methods above computationally predicted that c-Raf-RBD(RKY) would bind more tightly to KRasGTP than any other variant. The single-concentration screen using BLI also suggested that c-Raf-RBD(RKY) binds more tightly to KRasGTP than the previously reported best variant. The Kd values for the most promising variants were measured using a BLI assay with titration which confirmed the computational predictions that the novel construct c-Raf-RBD(RKY) is the highest affinity variant ever designed, with single-digit nanomolar affinity for KRasGTP.

Accordingly, on some aspects provided herein are novel KRas inhibitors. In some embodiments, the KRas inhibitor is A RAF proto-oncogene serine/threonine-protein kinase (c-RAF) mutant protein. In some embodiments, provided herein is a c-RAF mutant protein comprising one or more mutations in a receptor binding domain (RBD) of the protein. The mutation may be any suitable mutation, including a substitution mutation, a deletion mutation, or an insertion mutation. In some embodiments, the c-RAF mutant protein comprises a plurality of mutations. For example, the c-RAF mutant protein may comprise at least 1, at least 2, at least 3, at least 4, at least 5, or more than 5 mutations. In some embodiments, the one or more mutations are identified in Table 4. In some embodiments, the one or more mutations are identified in Table 3. In some embodiments, the one or more mutations comprise T57M, T57K, K87Y, V88Y, V88F, or a combination thereof.

In some embodiments, the c-RAF mutant protein comprises at least a V88Y mutation. In some embodiments, the c-RAF mutant protein comprises a V88Y mutation and one additional mutation. In some embodiments, the c-RAF mutant protein comprises a V88Y mutation and at least one additional mutation identified in Table 4. In some embodiments, the c-RAF mutant protein comprises a V88Y mutation and at least one additional mutation identified in Table 3. In some embodiments, the c-RAF mutant protein comprises V88Y, N71R, and A85K substitution mutations.

In some embodiments, provided herein are polynucleotides. In some embodiments, provided herein is a polynucleotide encoding a c-RAF mutant protein described herein. In some embodiments, provided herein are cells expressing one or more polynucleotides described herein. The cell may be any suitable cell, including prokaryotic and eukaryotic cells.

In some embodiments, provided herein are conjugates comprising the c-RAF mutant proteins described herein. For example, in some embodiments provided herein are conjugates comprising a c-RAF mutant protein and a cell targeting moiety. As used herein, the term "cell targeting moiety" refers to any moiety that facilitates targeted delivery of the conjugate to a desired cell. For example, a cell targeting moiety may facilitate targeting of the conjugate to a cell expressing a given cell surface receptor. In some embodiments, the cell targeting moiety may be a protein (e.g. antibody, antibody fragment), peptide, nucleic acid (e.g. aptamer), small molecule, or other moiety such as a vitamin or a carbohydrate.

As another example, in some embodiments provided herein are conjugates comprising a c-RAF mutant protein and a cell penetrating moiety. In some embodiments, the cell penetrating moiety is a cell penetrating peptide (CPP). Exemplary CPPs are described in Derakhshankhah, Biomedicine & Pharmacotherapy; Vol. 108 (2018) p. 1090-1096, Borelli et al., Molecules 2018, 23, 295, and Habault and Poyet, and Molecules 2019; 24(5): 927, the entire contents of each of which are incorporated herein by reference for all purposes In general, CPPs are short peptides that facilitate intake of molecules into a cell. In some embodiments, CPPs may facilitate uptake of the c-RAF mutant protein described herein into a desired cell, such as a cell within a subject. The CPP may be any suitable CPP, including cationic CPPs, amphipathic CPPs, and hydrophobic CPPs. The CPP may be synthetic. For example, polyarginine family CPPs are exemplary synthetic CPPs that may be used. The CPP may be protein-derived. For example, Transactivating transcriptional activator (TAT), and penetratin are protein-derived CPPs that may be used. The CPP may be chimeric, meaning that the CPP is composed of two or more motifs from dissimilar peptides. For example, transportan is a chimeric CPP derived from galanin and mastoparan.

CPPs that may be used for delivery of proteins, such as a c-RAF mutant protein described herein, into cells include polyarginine family CPPs (e.g. CPPs comprising a plurality of arginine residues, such as R6, R8, and R9) TAT or derivatives thereof, penetratin or derivatives thereof, pVEC, RRL helix, Shuffle, Penetramax, transportan or derivatives thereof, and the like. A comprehensive list of CPPs developed to date, along with cargo type (e.g. nucleic acid, proteins, peptides, nanoparticles, fluorophores, small molecule drugs, etc.) can be found at CPPsite 2.0, a publicly available database of cell-penetrating peptides incorporated herein by reference in its entirety for all purposes. Any of the CPPs described therein, in particular CPPs with demonstrated efficacy delivery protein or peptide cargo into cells, may be selected and used in conjugate described herein.

The CPP may be conjugated to the c-RAF mutant protein (e.g. the "cargo") by any suitable means, including covalent and non-covalent binding. Exemplary non-covalent conjugation methods include, for example, binding through electrostatic interactions.

A conjugate as described herein may be delivered to a subject for use in a method of treating cancer.

4. Methods Treating Cancer

In some aspects, provided herein are methods of treating cancer in a subject. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer is characterized by a KRas mutation. In some embodiments, the subject has or is at risk of developing a cancer associated with a KRas mutation selected from lung cancer (e.g. non-small cell lung cancer), colorectal cancer, or pancreatic cancer.

In some embodiments, the methods comprise providing to the subject a c-RAF mutant protein as described herein. In some embodiments, the methods comprise providing to the subject a conjugate comprising a c-RAF mutant protein as described herein. For example, the methods may comprise providing to the subject a conjugate comprising a CPP and a c-RAF mutant protein.

The c-RAF mutant protein or conjugate comprising the same may be formulated into a pharmaceutical composition comprising one or more pharmaceutically acceptable carriers (e.g. excipients). Selection of the appropriate carriers will depend on the mode of administration.

Contemplated routes of administration include oral, rectal, nasal, topical (including transdermal, buccal and sublingual), vaginal, parenteral (including subcutaneous, intramuscular, intravenous and intradermal) and pulmonary administration.

Therapeutic amounts (e.g. amounts of the antibiotic agent) are empirically determined and vary with the pathology being treated, the subject being treated and the efficacy and toxicity of the agent. It is understood that therapeutically effective amounts vary based upon factors including the age, gender, and weight of the subject, among others. It also is intended that the compositions and methods of this disclosure be co-administered with other suitable compositions and therapies for the treatment of cancer. For example, the compositions may be co-administered with radiation therapy, surgery, chemotherapy, targeted therapy, immunotherapy, stem cell transplant, hormone therapy, and the like.

The following Examples are provided by way of illustration and not by way of limitation.

EXAMPLES

Example 1

The K* algorithm provably approximates partition functions for a set of states (e.g., protein, ligand, and protein-ligand complex) to a user-specified accuracy $\varepsilon$. Often, reaching an $\varepsilon$-approximation for a particular set of partition functions takes a prohibitive amount of time and space. To alleviate some of this cost, two algorithms were developed for protein design: FRIES, a Fast Removal of Inadequately Energised Sequences, and EWAK*, an Energy Window Approximation to K*. In combination, these algorithms are shown herein to retain calculational accuracy while limiting the input sequence space and the conformations included in each partition function calculation to only the most energetically favorable. This combined approach lead to significant speed-ups compared to the previous state-of-the-art multi-sequence algorithm, BBK*.

Computational structure-based protein design (CSPD) is an innovative tool that enables the prediction of protein sequences with desired biochemical properties (such as improved binding affinity). OSPREY (Open Source Protein Redesign for You) [1] is an open-source, state-of-the-art software package used for CSPD. OSPREY's algorithms focus on provably returning the optimal sequences and conformations for a given input model. In contrast, stochastic, non-deterministic approaches [8-10] provide no guarantees on the quality of conformations, or sequences, and make determining sources of error in predicted designs very difficult [2-7].

When using OSPREY, the input model generally consists of a protein structure, a flexibility model (e.g., choice of sidechain or backbone flexibility, allowed mutable residues, etc.), and an all-atom pairwise-decomposable energy function that is used to evaluate conformations. OSPREY models amino acid sidechains using frequently observed rotational isomers or "rotamers" [11]. Additionally, OSPREY can also model continuous sidechain flexibility [12-15] along with discrete and continuous backbone flexibility [16-19], which allow for a more accurate approximation of protein behavior [13, 16, 20-23]. The output produced by CSPD generally consists of a set of candidate sequences and conformations. Many protein design methods have focused on computing a global minimum energy conformation (GMEC) [14, 18, 24-28]. However, a protein in solution exists not as a single, low-energy structure, but as a thermodynamic ensemble of conformations. Models that only consider the GMEC may incorrectly predict biophysical properties such as binding [12, 20-23, 29-31] because GMEC-based algorithms underestimate potentially significant entropic contributions.

In contrast to GMEC-based approaches, the K* algorithm [12, 29, 30] in OSPREY models thermodynamic ensembles to provably and efficiently approximate the K* score. The K* score is a ratio of the Boltzmann-weighted partition functions for a protein-ligand complex that estimates the association constant, $K_a$. BBK* [32] is the most recent improvement on the traditional K* algorithm that allows for multi-sequence design. Previous algorithms [12, 27, 29, 30, 33-35] that design for binding affinity using ensembles are linear in the size of the sequence space N, where N is exponential in the number of simultaneously mutable residue positions. BBK* is the first provable ensemble-based algorithm to run in time sublinear in N, making it possible not only to perform K* designs over large sequence spaces, but also to enumerate a gap-free list of sequences in order of decreasing K* score.

OSPREY has been used successfully on several empirical, prospective designs including de-signing enzymes [12, 16, 22, 29, 36], resistance mutations [2, 37, 38], protein-protein interaction inhibitors [30, 39], epitope-specific antibody probes [40], and broadly-neutralizing antibodies [41, 42]. These successes have been validated experimentally in vitro and in vivo and are now being tested in several clinical trials [43-45]. However, while OSPREY has been successful in the past, as the size of protein design problems grows (e.g., when considering a large protein-protein interface), enumerating and minimizing the necessary number of conformations and sequences to satisfy the provable halting criteria in previous K*-based algorithms [12, 29, 30] becomes prohibitive (despite recent algorithmic improvements [32]). The entire conformation space can be monumental in size and heavily populated with energetically unfavorable sequences and conformations. EWAK*, an Energy Window Approximation to K*, seeks to alleviate some of this difficulty by restricting the conformations included in each sequence's thermodynamic ensemble. EWAK* guarantees that each conformational ensemble contains all of the lowest energy conformations within an energy window of the GMEC for each design sequence. FRIES, a Fast Removal of Inadequately Energised Sequences, also mitigates this complexity problem by limiting the input sequence space to only the most favorable, low energy sequences.

Previous algorithms have focused on optimizing for sequences whose conformations are similar in energy to that of the GMEC. In contrast, FRIES focuses on optimizing for sequences with energies better-than or comparable-to the wild-type sequence. FRIES guarantees that the restricted input sequence space includes all of the sequences within an energy window of the wild-type sequence, but excludes any potentially unstable sequences with significantly worse partition function values. Wild-type sequences are generally expected to be near-optimal for their corresponding folds [46]. Therefore, limiting the sequence space to sequences energetically similar to or better than the wild-type sequence is reasonable. Compared to the previous state-of-the-art algorithm BBK*, FRIES and EWAK* improve runtimes by up to 2 orders of magnitude, FRIES decreases the size of the sequence space by up to more than 2 orders of magnitude, and EWAK* decreases the number of conformations included in partition function calculations by up to almost 2 orders of magnitude.

The K* algorithm's [12, 29, 30] K* score serves as an estimate of the binding constant, $K_a$, and is calculated by first approximating the Boltzmann-weighted partition function of each state: unbound protein (P), unbound ligand (L), and the bound protein-ligand complex (C). Each Boltzmann-weighted partition function $Z_x$ (s), $x \in \{P, L, C\}$, is defined by equation 1:

$$Z_x(s) = \sum_{d \in Q(s)} \exp(-E_x(d)/RT).$$

If s is any—generally amino acid—sequence of n residues, then Q(s) is the set of conformations defined by s, $E_x$(d) is the minimized energy of a conformation d in state x, and R and T are the gas constant and temperature, respectively. Many protein design algorithms approximate these partition functions for each state using either stochastic [49-52] or provable [2, 12, 29-31, 33, 52] methods.

OSPREY's K* algorithm provably approximates these partition functions to within a user-specified ε of the full partition function as defined in Eq (1). The binding affinity for sequence s is defined by equation 2:

$$K_a(s) = \frac{Z_C(s)}{Z_P(s)Z_L(s)}.$$

The K* algorithm provably approximates this binding affinity. This is enabled by the use of A*[4, 12, 26, 53], which allows for the gap-free enumeration of conformations in order of increasing lower bounds on energy [26]. However, enumerating a sufficient number of these conformations to obtain a guaranteed ε-approximation can be very time consuming because the set of all conformations Q(s) grows exponentially with the number of residues n. Also, the K* algorithm was originally [12, 29, 30] limited to computing a K* score for every sequence in the sequence space as defined by the input model for a particular design. However, BBK* [32] builds on K* and provably returns the top m sequences along with their ε-approximate K* scores and runs in time sublinear in the number of sequences. That is, BBK* does not require calculating ε-approximate K* scores for (or even examining) every sequence in the sequence space before it returns the top sequences. Nevertheless, BBK* may spend unnecessary time and resources evaluating unfavorable sequences before deciding to prune them.

To overcome the above limitations of BBK* and K*, FRIES, a Fast Removal of Inadequately Energised Sequences, and EWAK*, an Energy Window Approximation to K*, were developed. These two algorithms focus on limiting the input sequence space and the number of conformations included in each partition function estimate when approximating a sequence's K* score to provably only the most energetically favorable options. The FRIES/EWAK* approach limits the number of conformations that must be enumerated, which leads to significant speed-ups because each enumerated conformation must undergo an energy minimization step. This minimization step is relatively expensive, therefore, anything that reduces the number of minimized conformations while not sacrificing provable accuracy is desirable. For the importance of this minimization step to biological accuracy, see the discussions of continuous flexibility and its comparison to discrete flexibility in [4, 5, 7, 13, 14, 19]. EWAK* also maintains the advances made by BBK* including running in time sublinear in the number of sequences N and returning sequences in order of decreasing K* score. FRIES and EWAK* are described in further detail below.

Computational Materials and Methods

Algorithms:

Fast Removal of Inadequately Energised Sequences (FRIES)

Generally in protein design when optimizing a protein-protein interface (PPI) for affinity, the designer aims to improve the K* score of a variant sequence relative to the wild-type sequence, and, when performing a design targeting a similar fold, to minimally perturb the native structure. To accomplish this, FRIES guarantees to only keep sequences whose partition function values are not markedly worse than the wild-type sequence's partition function values for all of the design states (e.g. protein, ligand, and complex). How many orders of magnitude worse a particular sequence's partition function values are allowed to be is determined by a user-specified value m. The FRIES algorithm prunes sequences that exhibit massive decreases in partition function values that signal an increased risk of disturbing the native structure of the states in a given system. However, sequences with markedly worse, lower partition function values may be required when searching for, for example, resistance mutations, where positive and negative design are necessary [2, 37, 38]. FRIES does still allow for sequences that may have lower, worse partition function values by allowing the user to specify how many orders of magnitude lower a candidate sequence's partition function is allowed to be relative to the wild-type sequence's partition function.

To prune the input sequence space, FRIES exploits A* over a multi-sequence tree (as is described and used in COMETS [55]), which enjoys a fast sequence enumeration in order of lower bound on minimized energy. Each sequence v in this multi-sequence tree [55] has a corresponding single-sequence conformation tree, viz., a tree that can be searched for the lowest energy conformations for a sequence v. FRIES first enumerates sequences (in order of energy lower bounds) in the multi-sequence tree until the wild-type sequence is found. Then, FRIES searches the wild-type's corresponding single-sequence conformation tree using A*. The first conformation enumerated according to monotonic lower bound on pairwise minimized energy is then subjected to a full-atom minimization [30] to calculate the minimized energy of one of the wild-type sequence's conformations $E_{WT}$. FRIES then continues enumerating sequences in the multi-sequence tree in order of increasing lower bound on minimized energy until the lower-bound on the energy of a sequence v, $E_v^e$, is greater than $E_{WT}+w$ where $E_{WT}$ is as described above and w is a user-specific energy window value. Any variant sequence v with a lower bound on minimized energy $E_v^e$ not satisfying the following criterion is pruned:

$$E_v^e \leq E_{WT}+w. \quad \text{(equation 3)}$$

This criterion guarantees that the remaining, unpruned sequence space includes all sequences within an energy window of the wild-type sequence's energy. Therefore, it calculates an upper bound $q^\oplus$ on the partition function for each sequence v by Boltzmann-weighting the lower bound on its energy $E_v^e$ and multiplying it by the size of the conformation space for that particular sequence $|Q(v)|$:

$$q_v^\oplus = |Q(v)|\exp(-E_v^e/RT). \quad \text{(equation 4)}$$

The lower bound for the wild-type sequence $q_{WT}^e$ is calculated by Boltzmann-weighting the minimized energy of the single conformation found during the sequence search for the wild-type sequence $E_{WT}$.

$$q_{WT}^e = \exp(-E_{WT}/RT). \quad \text{(equation 5)}$$

$q_{WT}^e$ is a lower bound because, in the worst case, at least this one conformation will contribute to the partition function for the wild-type sequence. FRIES then uses these bounds to remove all of the sequences whose partition function value is not within some user-specified m orders of magnitude of the lower bound on the wild-type partition function $q_{WT}^e$. If the following criterion is not met, the sequence v is pruned from the space:

$$\ln q_v^\oplus \leq \ln q_{WT}^e + m. \quad \text{(equation 6)}$$

FRIES prunes sequences for the protein, the ligand, and the protein-ligand complex independently, limiting the input sequence space to exclude unfavorable sequences for all of the states. The resulting smaller sequence space is subsequently used as input for EWAK*. The set of sequences remaining is guaranteed to include all of the sequences within a user-specified energy window w of the wild-type sequence that also satisfy the partition function criterion given in Eq (4). FRIES can be used to limit the size of the input sequence space in this fashion for any of the protein design algorithms available within OSPREY.

Energy Window Approximation to K* (EWAK*)

After reducing the size of the input sequence space using FRIES, EWAK* proceeds by using a variation on an existing algorithm: BBK* (described in [32]). The crucial difference between BBK* and EWAK* is that with EWAK* the ensemble of conformations used to approximate each K* score is limited to those within a user-specified energy window of the GMEC for each sequence. This guarantees to populate the partition function for a particular sequence and state with all of the provably lowest, most-favorable conformations (that fall within the user-specified energy window). These conformations often account for the majority of the full ε-approximate partition function in traditional K* calculations [12]. Hence, EWAK* also empirically enjoys negligible loss in accuracy of K* scores. EWAK* retains the beneficial aspects of BBK*, including returning sequences in order of decreasing predicted binding affinity and running in time sublinear in the number of sequences.

Computational Experiments

FRIES/EWAK* was implemented in the OSPREY suite of open source protein design algorithms [1]. FRIES was tested on 2,662 designs that range from an input sequence space size of 441 to 10,164 total sequences. The size of the reduced input sequence space produced by FRIES was compared to the size of the full input sequence space size for each design. For these tests, FRIES returned every sequence within 8 kcal/mol of the wild-type sequence and was set to include only those sequences that are at most 2 orders of magnitude worse in partition function value than the wild-type. Computational experiments were also run comparing FRIES/EWAK* with the previous state-of-the-art algorithm in OSPREY: BBK*[32]. Using BBK* and FRIES/EWAK*, the top 5 best binding sequences for 167 different designs were computed to compare the running time of BBK* vs. FRIES/EWAK*. FRIES was limited to sequences within 4 kcal/mol of the wild-type sequence that are at most 2 orders of magnitude worse in partition function values than the wild-type. The EWAK* partition function approximations were limited to conformations within an energy window of 1 kcal/mol of the GMEC for each sequence.

BBK* was set to return the top 5 sequences with an accuracy of ε=0.68 (as was described in [32]). Using these same EWAK* and BBK* parameters, the change in the size of the conformation space necessary to compute an accurate K* score for BBK* vs. EWAK* for 661 partition functions from 161 design examples was compared. The number of conformations that undergo minimization (as described in [12-15]) for each partition function calculation with EWAK* was also compared across different energy window sizes for 350 partition function calculations from 87 design examples. These partition function calculations were compared to BBK*'s partition function calculations with a demanded accuracy of ε=0.10. This smaller ε allowed for more accurate approximations of the K* scores.

Every design included a set of mutable residues along with a set of surrounding flexible residues (see FIG. 1 for an example). All of these residues were allowed to be continuously flexible [12-15]. The designs were selected from 40 different protein structures (listed in Table 1 and also used in [32, 56]), and were run on 40-48 core Intel Xeon nodes with up to 200 GB of memory.

TABLE 1

Protein structures used in computational experiments

| PDB ID | Molecule(s) |
|---|---|
| 2RL0 | Fibronectin and Fibronectin-binding protein |
| 4WEM | K88 fimbrial protein AC and Anti-F4 + ETEC bacteria VHH variable region |
| 2P4A | Ribonuclease pancreatic and ANTIBODY CAB-RN05 |
| 2RFE | Epidermal growth factor receptor and ERBB receptor feedback inhibitor 1 |
| 2RF9 | Epidermal growth factor receptor and ERBB receptor feedback inhibitor 1 |
| 4WWI | Immunoglobulin G-binding protein A and Ig gamma-3 chain C region |
| 4ZNC | Immunoglobulin G-binding protein A and Ig gamma-3 chain C region |
| 3U7Y | NIH45-46 heavy chain, Ig gamma-1 chain C region, Envelope glycoprotein gp160, and NIH45-46 light chain, Ig kappa chain C region |
| 2HNV | Oxytocin-neurophysin 1 |
| 4Z80 | EGF family domain-containing protein and Cytoadherence-linked asexual protein |
| 4U3S | Cellulosomal scaffolin adaptor protein B and Cellulosomal scaffolidin |
| 1B6C | FK-506-BINDING PROTEIN and TGF-B SUPERFAMILY RECEPTOR TYPE I |
| 3GXC | Ephrin type-A receptor 4 and Ephrin-B2 |
| 1GWC | GLUTATHIONE S-TRANSFERASE TSI-1 |
| 4WYU | Protein scribble homolog and peptide SER-TRP-PHE-GLN-THR-ASP-LEU |
| 5IT3 | Lysine-specific histone demethylase 1A |

TABLE 1-continued

Protein structures used in computational experiments

| PDB ID | Molecule(s) |
|---|---|
| 2HNU | Oxytocin-neurophysin 1 |
| 5D68 | Krey interaction trapped protein 1 |
| 5A6Y | FUCOSE-BINDING LECTIN PA-IIL. |
| 3K3Q | Llama Aa1 VHH domain and Botulinum neurotoxin type A |
| 3CAL | Fibronectin and peptide from Fibronectin-binding protein A |
| 1A0R | TRANSDUCIN (BETA SUBUNIT), TRANSDUCIN (GAMMA SUBUNIT), and PHOSDUCIN |
| 5EM2 | Ribosome biogenesis protein ERB1 and Ribsome biogenesis protein YTM1 |
| 4PXF | Rhodopsin and S-arrestin |
| 3EB6 | Baculoviral IAP repeat-containing protein 3 and Ubiquitin-conjugating enzyme E2 D2 |
| 3BU8 | Telomeric repeat-binding factor 2 and TERF1-interacting nuclear factor 2 |
| 5DC0 | Fibronectin and Tyrosine-protein kinase ABL1 |
| 2Q1E | Amyloidogenic immunoglobulin light chain protein AL-09 |
| 2XXM | CAPSID PROTEIN P24, CAMEL ID VHH 9, and INHIBITOR OF CAPSID ASSEMBLY |
| 2Q2A | ArtJ |
| 2RFD | Epidermal growth factor receptor and ERBB receptor feedback inihibitor 1 |
| 5DC4 | Tyrosine-protein kinase ABL1 and AS25 monobody |
| 2XGY | RELIK CAPSID N-TERMINAL DOMAIN and PEPTIDYL-PROLYL CIS-TRANS ISOMERASE A |
| 2P49 | Ribonuclease pancreatic and ANTIBODY CAB-RN05 |
| 3RJQ | C186 gp120 and Llama VHH A12 |

Each protein structure has its PDB ID listed along with its molecule names as presented in the Protein Database entry for each structure. Individual designs are not listed or described here, but the necessary code and data is provided for the interested reader (see Data availability).

Computational Results:

Fries can Reduce the Size of the Input Sequence Space by More than 2 Orders of Magnitude while Retaining the Most Favorable Sequences:

The number of remaining sequences after FRIES was compared to the size of the complete input sequence space. In the best case, when using FRIES, the sequence space was decreased by more than 2 orders of magnitude and the conformation space was decreased by just over 4 orders of magnitude. The sequence space was reduced an average of 49% and the conformation space was reduced an average of 40%. These results are broken down further in FIG. 3.

Fries/EWAK* is Up to 2 Orders of Magnitude Faster than BBK*:

The overall runtime was compared between BBK* and FRIES/EWAK*. FRIES/EWAK* was an average of 62% faster than BBK* on 167 example design problems. FRIES removed unfavorable sequences from the search space for 156 out of the 167 design problems. FRIES/EWAK* performed consistently faster than BBK* (in 92% of the design examples) as shown in FIG. 4, Panel A. The longest running BBK* design problem took nearly 8 days, whereas FRIES/EWAK* completed the same example in just under 2 hours. In contrast, the design problem that took the longest for FRIES/EWAK* out of the 167 tested only required about 22 hours (the same design took BBK* just over 178 hours).

EWAK* Limits the Number of Minimized Conformations when Approximating Partition Functions while Maintaining Accurate K* Scores:

661 K* score calculations were examined. The total number of conformations minimized to approximate the K* score was decreased by an average of 27%. In the best case the number of conformations minimized to approximate the K* score was decreased by 93%. These results are plotted in FIG. 4, Panel B. Even though the partition function approximations were limited to a smaller conformation space with EWAK*, the K* scores did not differ by more than 0.2 orders of magnitude between EWAK* and BBK* for these 661 example K* score calculations. A total of 350 of these 661 partition functions were subsequently re-estimated using BBK* with a more accurate, stringent ε value of 0.1 and using EWAK* with varied energy windows: 1.0 kcal/mol, 3.0 kcal/mol, and 5.0 kcal/mol. The number of conformations minimized for each complex partition function calculation across the examples was examined. When using 1.0 kcal/mol, EWAK* minimized up to 1.7 orders of magnitude fewer conformations (see FIG. 4, Panel C for more details). Despite this decrease in the number of included conformations, EWAK* reported accurate K* scores. The largest difference in scores between BBK* and EWAK* was 0.3 orders of magnitude. The accuracy of EWAK* is explored further below.

Example 2

Overview:

As a proof of concept to test these algorithms and the design approach, FRIES and EWAK* were used to study the protein-protein interface (PPI) of KRas GTP in complex with its tightest-binding effector, c-Raf. KRas is an important cancer target that has historically been considered "undruggable" [47]. Deepening the understanding of the PPI between KRas and its effectors is an important step toward developing effective new therapeutics. For this study, the focus was on the re-design of the c-Raf Ras-binding domain (c-Raf-RBD) in complex with $KRas^{GTP}$ (c-Raf-RBD:$KRas^{GTP}$). First, the new algorithms described herein successfully retrospectively predicted the effect on binding of mutations in the c-Raf-RBD:$KRas^{GTP}$ PPI even where other computational methods previously failed [48]. Next, FRIES/EWAK* were used prospectively to predict the effect of novel, previously unreported mutations in the PPI of the c-Raf-RBD:$KRas^{GTP}$ complex. The binding of top OSPREY-predicted c-Raf-RBD variants to KRas was subsequently measured using a bio-layer interferometry (BLI) assay single-concentration screen. This screen suggested that one of the new computationally-predicted c-Raf-RBD variants—c-Raf-RBD(Y), a c-Raf-RBD that includes the mutation V88Y—exhibits improved binding to $KRas^{GTP}$.

Next, a c-Raf-RBD variant, c-Raf-RBD(RKY), was created, that included this new mutation, V88Y, together with two previously reported mutations [48], N71R and A85K. FRIES/EWAK* computationally predicted that c-Raf-RBD (RKY) would bind more tightly to $KRas^{GTP}$ than any other variant. The single-concentration screen using BLI also suggested that c-Raf-RBD(RKY) binds more tightly to $KRas^{GTP}$ than the previously reported best variant [48]. The $K_d$ values for the most promising variants were measured using a BLI assay with titration which confirmed computational predictions and that the novel construct c-Raf-RBD (RKY) is the highest affinity variant ever designed, with single-digit nanomolar affinity for $KRas^{GTP}$.

Computational Redesign of the c-Raf-RBD:KRas Protein-Protein Interface:

The biological accuracy of the new modules FRIES and EWAK* after adding them to OSPREY was tested in the case of a particular system: c-Raf-RBD in complex with KRas. The c-Raf Ras-binding domain (c-Raf-RBD) is a small self-folding domain that does not include the kinase signaling domains normally present in c-Raf. The c-Raf-RBD normally binds to KRas when KRas is GTP-bound (KRas(IP). A c-Raf-RBD variant that has high affinity for KRas GTP could be an important first step toward discovering a tool that disrupts the KRas:effector interaction. Despite the recent successes with inhibitors targeting mutant KRas(G12C) by trapping it in the inactive GDP-bound state [57-62] and their recent move to clinical trials [63], these inhibitors are susceptible to resistance in the form of up-regulation of guanine nucleotide exchange factors (GEFs) and nucleotide exchange [60] which both push KRas to remain in its GTP-bound state. An inhibitor of the interaction between KRas$^{GTP}$ and its effectors is hypothesized to have the advantage of not being susceptible to these mechanisms of resistance because it would directly interrupt KRas signaling. Hence, to further verify the accuracy and utility of FRIES/EWAK*, the focus was placed on this important PPI between KRas$^{GTP}$ and one of its many effectors, c-Raf.

First, previously reported mutations in the c-Raf-RBD [48, 64, 65] and how they affect the binding of c-Raf-RBD to KRas were investigated. This retrospective study laid the groundwork for the prospective study presented herein that investigates novel mutations. Following the retrospective study, =the PPI was computationally redesigned using FRIES/EWAK* in search of new c-Raf-RBD variants with improved affinity for KRas$^{GTP}$. To perform these computational designs, a homology model of c-Raf-RBD bound to KRas$^{GTP}$ was first made.

Figure 5:
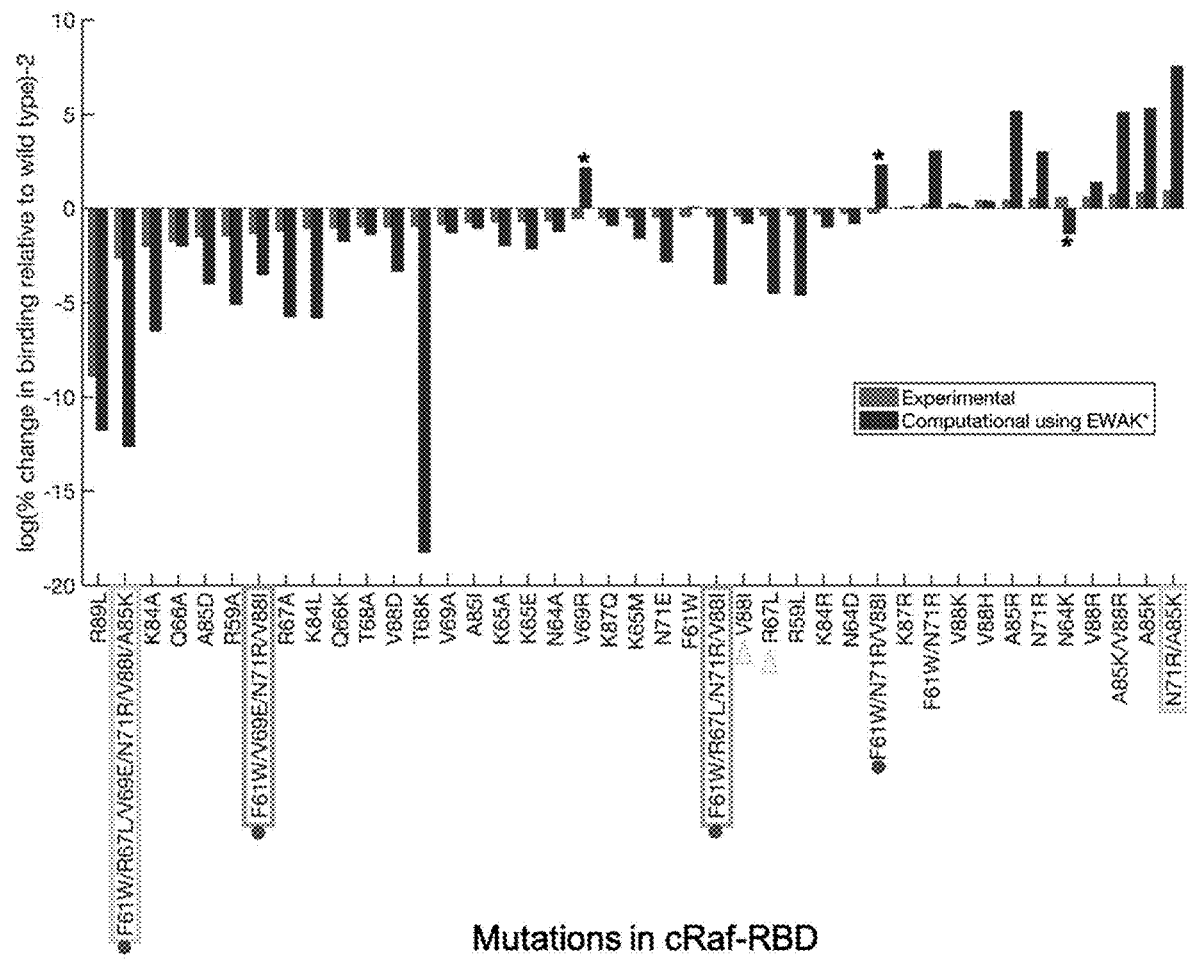
FIG. 5 shows the predicting the effect of mutations in c-Raf-RBD on binding with KRas in accordance with one embodiment of the present disclosure. Each bar represents either the experimental or computationally predicted affect each variant has on binding. The bars are sorted in increasing order of Δb value of the experimental bars. If the Δb value is less than 0, binding decreases. If the Δb value is greater than 0, binding increases. If the Δb value is close to 0, the effect is neutral. Quantitative values of K* tend to overestimate the biological effects of mutations (leading to the much larger predicted bars) due to the limited nature of the input model compared to a biologically accurate representation. However, K* in general does a good job ranking variants, as can be seen here in FIG. 6, in [1], and in [38]. Out of the 41 variants listed on the x-axis, only 3 were predicted incorrectly (marked with black asterisks) by EWAK*. In terms of accuracy, BBK* performed very similarly to EWAK*(data not shown), however, in 2 cases (the second case and the last case on the x-axis, respectively, marked with boxes), BBK* ran out of memory and was unable to calculate a score. BBK* also did not return values for the 2 other variants marked with boxes. The variants marked with dots were tested in [48] experimentally—not computationally—and decreased binding of c-Raf-RBD to $KRas^{GTP}$ was observed, which EWAK* was able to predict correctly. The two variants marked with triangles were computationally predicted in [48] to improve binding of c-Raf-RBD to $KRas^{GTP}$. However, the experimental validation in [48] showed that these variants exhibit decreased binding, which EWAK* accurately predicted.

FRIES/EWAK* Retrospectively Predicted the Affect Mutations in c-Raf-RBD have on Binding to KRas:

Each previously reported c-Raf-RBD variant [48, 64, 65] was tested computationally using FRIES/EWAK* by calculating a K* score, a computational approximation of $K_a$, for each variant along with its corresponding wild-type sequence. A percent change in binding was then calculated by comparing the variant's K* score to the corresponding wild-type sequence's K* score. The $\log_{10}$ of this value was then calculated and normalized to the wild-type by subtracting 2. A similar procedure was completed using the reported experimental data in order to easily compare the computationally predicted effect with the experimentally measured effect. The resulting value, called Δb, represents the change in binding. If a variant has a Δb less than 0, it is predicted to decrease binding. If a variant has a Δb greater than 0, it is predicted to increase binding. Δb values that are roughly equivalent to 0 indicate variants that have little to no effect on binding since the wild-type sequence was normalized to 0. The Δb values for the 41 computationally tested variants were plotted and compared to experimental values in FIG. 5.

Figure 6:
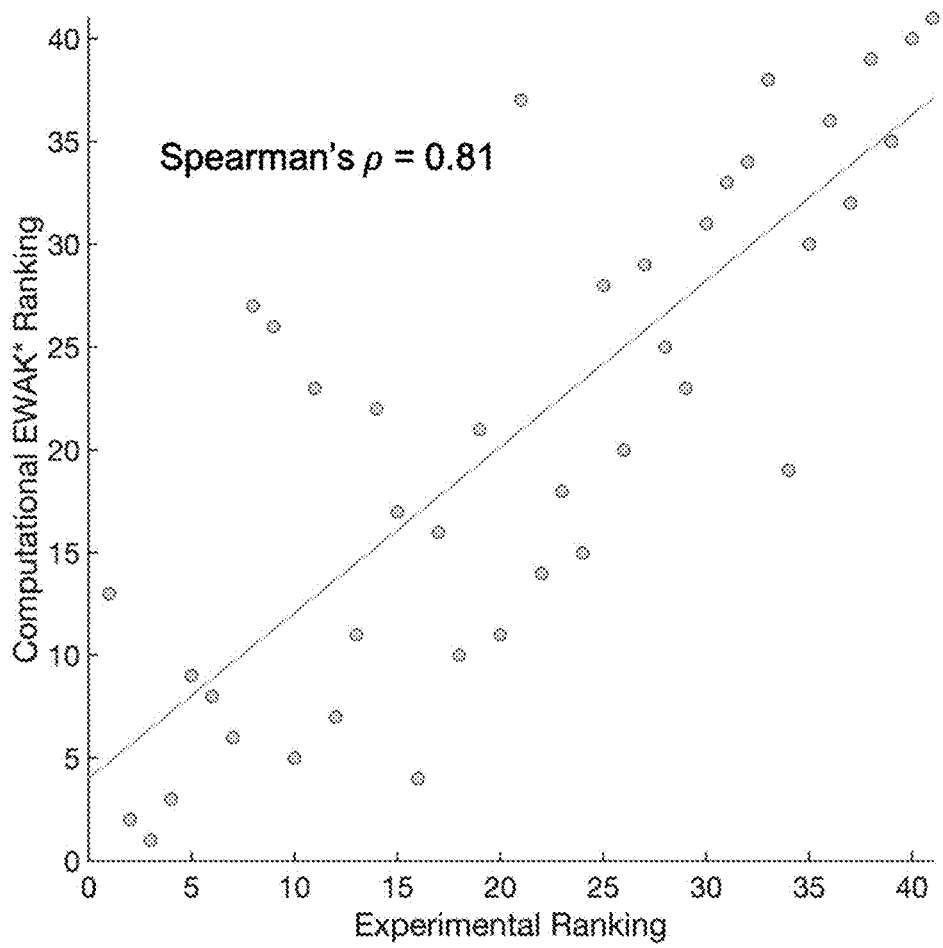
FIG. 6 shows the comparison of the computational EWAK* ranking with the experimental ranking for 41 c-Raf-RBD variants binding to KRas in accordance with one embodiment of the present disclosure. Each dot represents a variant of c-Raf-RBD and is plotted according to the experimental ranking along with the corresponding computational ranking of its binding to KRas. A least squares fit line is shown in gray. Calculating the Pearson correlation coefficient between the two sets of rankings yields a Spearman's ρ of 0.81.

Out of the 41 variants tested (see Table 2), EWAK* predicted the experimentally-reported effect (increased vs. decreased binding) correctly in 38 cases. The three designs where the effect was predicted incorrectly are marked with a star in FIG. 5. To make these predictions, the corresponding computational designs ranged in size from single point mutations up to 6 simultaneous mutations. Results are outlined in FIG. 5. Furthermore, the Spearman's ρ value—a measure of the correlation between two sets of rankings—when comparing the experimental data to the computational predictions is 0.81. This ρ value indicates that not only can EWAK" correctly predict the effect of a particular set of mutations, but that EWAK* also does a good job ranking the variants in order according to change in binding upon mutation (see FIG. 6). This value is very similar to Spearman's ρ values for other PPI systems when using OSPREY [1].

TABLE 2

Experimental and computational percent change in binding and rankings.

| Mutation(s) | Exp. (%) | Comp. (%) | Exp. Ranking | Comp. Ranking |
|---|---|---|---|---|
| Wild-Type | 100.00 | 100.00 | N/A | N/A |
| R89L | $1.3 \times 10^{-7}$ | $1.64 \times 10^{-10}$ | 1 | 3 |
| F61W/R67L/V69E/N71R/V88I/A85K | 0.23 | $2.20 \times 10^{-11}$ | 2 | 2 |
| K84A | 0.93 | $3.03 \times 10^{-5}$ | 3 | 4 |
| Q66A | 1.76 | 0.99 | 4 | 16 |
| A85D | 3.00 | 0.01 | 5 | 10 |
| R59A | 3.42 | $8.09 \times 10^{-4}$ | 6 | 7 |
| F61W/V69E/N71R/V88I | 4.64 | 0.03 | 7 | 12 |
| R67A | 6.19 | $1.78 \times 10^{-4}$ | 8 | 6 |
| K84L | 8.60 | $1.56 \times 10^{-4}$ | 9 | 5 |
| Q66K | 9.00 | 1.78 | 10 | 18 |
| T68A | 10.00 | 4.03 | 11 | 20 |
| V88D | 10.00 | 0.05 | 12 | 13 |
| T68K | 11.00 | $5.63 \times 10^{-17}$ | 13 | 1 |
| V69A | 13.68 | 5.08 | 14 | 22 |
| A85I | 18.00 | 8.64 | 15 | 24 |
| K65A | 18.57 | 1.04 | 16 | 17 |
| K65E | 19.40 | 0.71 | 17 | 15 |
| N64A | 21.31 | 5.77 | 18 | 23 |
| V69R | 29.00 | $1.40 \times 10^{4}$ | 19 | 34 |
| K87Q | 30.00 | 12.43 | 20 | 26 |
| K65M | 31.71 | 2.53 | 21 | 19 |
| N71E | 34.00 | 0.15 | 22 | 14 |
| F61W | 36.11 | 116.20 | 23 | 29 |
| F61W/R67L/N71R/V88I | 36.11 | 0.01 | 24 | 11 |
| V88I | 39.39 | 16.15 | 25 | 28 |
| R67L | 42.00 | $3.06 \times 10^{-3}$ | 26 | 9 |
| R59L | 43.00 | $2.51 \times 10^{-3}$ | 27 | 8 |
| K84R | 49.00 | 10.01 | 28 | 25 |
| N64D | 50.00 | 15.60 | 29 | 27 |
| F61W/N71R/V88I | 54.17 | $1.96 \times 10^{4}$ | 30 | 35 |
| K87R | 100.00 | 120.04 | 31 | 30 |
| F61W/N71R | 162.50 | $1.10 \times 10^{5}$ | 32 | 37 |
| V88K | 171.00 | 127.37 | 33 | 31 |
| V88H | 266.00 | 227.92 | 34 | 32 |
| A85R | 290.00 | $1.50 \times 10^{7}$ | 35 | 39 |
| N71R | 325.00 | $9.97 \times 10^{4}$ | 36 | 36 |
| N64K | 380.00 | 4.47 | 37 | 21 |
| V88R | 400.00 | $2.44 \times 10^{3}$ | 38 | 33 |
| A85K/V88R | 550.00 | $1.33 \times 10^{7}$ | 39 | 38 |
| A85K | 700.00 | $2.13 \times 10^{7}$ | 40 | 40 |
| N71R/A85K | 866.67 | $3.63 \times 10^{9}$ | 41 | 41 |

For each listed variant, the experimental percent change in binding relative to wild-type as reported in and as calculated from reported binding values in and [48], the EWAK* computationally predicted percent change in binding, and the rankings that correspond to these values are given. The rankings have a Pearson correlation of 0.81.

BBK* produced similarly accurate results, but took up to 10 times longer and failed to produce results in 4 cases. In particular, in 2 cases (the second from the left and the far right on the x-axis, marked in boxes in FIG. 5), BBK* ran out of memory. These cases serve as examples of large designs where EWAK* outperforms BBK*. In the 2 other cases (the other boxes in FIG. 5), BBK* failed to return a result for the requested sequence in the top 5 reported sequences. This illustrated how EWAK* and FRIES are particularly helpful when performing these types of bigger designs that contain more simultaneous mutations and more flexible residues.

Next, predictions using the novel algorithms described herein were compared to the interesting biological predictions in [48]. It is unclear how many mutants were computationally evaluated, but the authors do report computational predictions for 6 point mutations. Of those, point mutants R67L, N71R, and V88I were predicted to improve the intermolecular interactions between c-Raf-RBD and KRas$^{GTP}$. However, experiments found that R67L and V88I actually reduced the binding of c-Raf-RBD to KRas$^{GTP}$ [48, 64]. In contrast to [48], EWAK* accurately predicted that these mutations decrease binding of c-Raf-RBD to KRas$^{GTP}$. For a more detailed view of one of these designs, V88I, see FIG. 7. Additionally, a number of mutations were combined and experimentally tested in [48]. Unfortunately, none of these variants improved binding to either KRas$^{GTP}$ or KRas$^{GDP}$, which FRIES/EWAK* correctly predicted computationally (see FIG. 5). In [48], the authors do not present any computational predictions for these combined variants, but the results herein show that a computational prediction using OSPREY's EWAK* would have saved the time and resources taken to experimentally test these variants.

Prospective Redesign of the c-Raf-RBD:KRas Protein-Protein Interface Toward Improved Binding:

The ability to accurately predict the effect mutations have on the binding of c-Raf-RBD to KRas$^{GTP}$ gave confidence in the EWAK* algorithm's ability to predict new mutations in this interface toward a c-Raf-RBD variant that exhibits an even higher affinity for KRas$^{GTP}$ than previously reported variants which focused on targeting KRas$^{GDP}$ [48]. Therefore, to do a prospective study, 14 positions in c-Raf-RBD in the c-Raf-RBD:KRas PPI were computationally redesigned to identify promising mutations. After extending OSPREY to include FRIES and EWAK*, 14 different designs were completed where each design included 1 mutable position that was allowed to mutate to all amino acid types except for proline. Each design also included a set of surrounding flexible residues within roughly 4 angstrom of the mutable residue. These designs were run using FRIES and EWAK* and included continuous flexibility [12-15].

FRIES was first used to limit each design to only the most favorable sequences and then EWAK* was used to estimate the K* scores. The upper and lower bounds on the EWAK* score for each design are reported in Table 3 and Table 4, where the listed sequences are those that were not pruned during the FRIES step. From these results, the predicted binding effect (increased vs. decreased) was determined based on comparing each variant's K* score to its corresponding wild-type K* score. 5 novel point mutations—that are not believed to be reported in any existing literature—were selected for experimental validation (see Table 3). It is worth noting that these 5 point mutations were selected out of an initial 294 possible mutations. Experimental validation was limited to only these 5 new mutations and 2 previously reported mutations. This greatly reduced the amount of resources necessary for experimental validation compared to testing all 294 possibilities. These mutations were selected based on having a promising K* score and through examining structures calculated by EWAK*. Of the mutations selected, T57M was selected to act as a variant that was computationally predicted to be comparable to wild-type. This variant was included to further verify the accuracy of OSPREY's predictions. On the other hand, some of OSPREY's top predictions were excluded, for instance, T57R (included in Table 4) was not selected for experimental testing because it has an unsatisfied hydrogen bond as evidenced in the structures calculated by OSPREY. Therefore, it is not believed that the score accurately represents the effect the mutation will have. Other excluded top predictions (see Table 4) displayed similar characteristics or have been reported and tested previously [48, 64, 65].

TABLE 3

Table of computational results using OSPREY/FRIES/EWAK* selected for experimental validation.

| Mutation | Lower Bound log (K*) | Upper Bound log (K*) |
|---|---|---|
| T57M | 3.43 | 3.46 |
| T57 | 3.82 | 3.92 |
| T57K | 5.01 | 5.07 |
| N71 | 7.25 | 7.49 |
| N71R | 9.66 | 10.10 |
| A85 | 26.29 | 26.85 |
| A85K | 30.67 | 32.30 |
| K87 | 13.42 | 14.14 |
| K87Y | 14.06 | 14.24 |
| V88 | 16.46 | 16.61 |
| V88Y | 17.34 | 17.55 |
| V88F | 17.99 | 18.15 |

Each section of the table shows the results of the redesign of a residue position in c-Raf-RBD in the c-Raf-RBD:KRas PPI in order of increasing upper bound on log(K*) that were also selected for experimental validation (all of the computational results are listed in Table 4). The table contains the values for upper and lower bounds on log(K*) values (these bounds are described in detail in [32]). The two residues N71R and A85K are the best previously discovered [48] mutations that improve binding (independently and additively) and are included in the tightest binding variant, c-Raf-RBD(RKY) (see FIGS. 8, 9, and 10). Mutations T57K, K87Y, V88Y, and V88F were selected for experimental testing and validation. The T57M variant was also selected for testing to act as a mutation predicted to be comparable to wild-type to test how accurately OSPREY predicted the effects of these mutations.

TABLE 4

Table of computational predictions for point mutants in c-Raf-RBD.

| Mutation | Lower Bound log(K*) | Upper Bound log (K*) |
|---|---|---|
| T57E | 1.47 | 1.50 |
| T57D | 2.05 | 2.07 |
| T57G | 3.34 | 3.35 |
| T57Q | 3.38 | 3.42 |
| T57M† | 3.43 | 3.46 |
| T57A | 3.47 | 3.48 |
| T57S | 3.45 | 3.53 |
| T57F | 3.61 | 3.63 |
| T57C | 3.63 | 3.66 |
| T57Y | 3.60 | 3.66 |
| T57L | 3.68 | 3.71 |
| T57N | 3.71 | 3.77 |
| T57Hid | 3.72 | 3.81 |
| T57V | 3.78 | 3.81 |
| T57I | 3.86 | 3.90 |
| T57* | 3.82 | 3.92 |
| T57W | 3.97 | 4.02 |
| T57Hie | 4.22 | 4.26 |
| T57K† | 5.01 | 5.07 |
| T57R | 5.03 | 5.12 |
| T57Hip | 5.62 | 5.70 |
| R59D | 9.48 | 9.74 |
| R59E | 10.30 | 10.64 |
| R59G | 12.94 | 13.03 |
| R59A | 12.96 | 13.06 |
| R59N | 12.88 | 13.10 |
| R59V | 13.01 | 13.11 |
| R59C | 12.96 | 13.14 |
| R59S | 12.88 | 13.15 |
| R59F | 12.96 | 13.15 |
| R59Y | 12.99 | 13.18 |
| R59T | 12.96 | 13.25 |
| R59I | 13.06 | 13.29 |

TABLE 4-continued

Table of computational predictions for point mutants in c-Raf-RBD.

| Mutation | Lower Bound log(K*) | Upper Bound log (K*) |
|---|---|---|
| R59Hid | 13.03 | 13.35 |
| R59L | 13.42 | 13.58 |
| R59M | 13.28 | 13.68 |
| R59Q | 13.55 | 13.74 |
| R59W | 13.93 | 14.04 |
| R59Hie | 13.88 | 14.25 |
| R59Hip | 15.86 | 16.21 |
| R59K | 16.02 | 16.58 |
| R59* | 17.85 | 18.30 |
| K65T | 6.94 | 7.91 |
| K65G | 8.46 | 8.89 |
| K65D | 8.47 | 9.08 |
| K65A | 8.73 | 9.10 |
| K65E | 8.56 | 9.11 |
| K65L | 8.91 | 9.38 |
| K65S | 8.79 | 9.38 |
| K65I | 9.13 | 9.52 |
| K65N | 9.06 | 9.55 |
| K65C | 9.05 | 9.57 |
| K65Q | 9.04 | 9.57 |
| K65F | 9.06 | 9.68 |
| K65M | 9.09 | 9.70 |
| K65Y | 9.10 | 9.77 |
| K65Hip | 9.40 | 9.88 |
| K65W | 9.21 | 9.90 |
| K65Hid | 9.36 | 9.92 |
| K65Hie | 9.42 | 10.02 |
| K65R | 10.46 | 11.31 |
| K65* | 10.62 | 11.48 |
| Q66Hie | 2.76 | 2.82 |
| Q66Hip | 3.17 | 3.23 |
| Q66L | 7.17 | 7.25 |
| Q66E | 7.93 | 7.95 |
| Q66Hid | 8.64 | 8.71 |
| Q66D | 11.37 | 11.42 |
| Q66A | 11.44 | 11.48 |
| Q66G | 11.02 | 11.57 |
| Q66S | 11.59 | 11.71 |
| Q66K | 11.63 | 11.81 |
| Q66N | 11.79 | 11.85 |
| Q66R | 11.87 | 11.96 |
| Q66C | 12.43 | 12.47 |
| Q66T | 12.39 | 12.48 |
| Q66M | 12.65 | 12.73 |
| Q66* | 13.43 | 13.49 |
| R67Y | 7.88 | 8.43 |
| R67E | 8.58 | 9.11 |
| R67D | 8.44 | 9.21 |
| R67W | 9.28 | 9.62 |
| R67F | 10.74 | 11.14 |
| R67Hie | 11.62 | 12.31 |
| R67G | 12.14 | 12.39 |
| R67A | 12.37 | 12.61 |
| R67S | 12.33 | 12.98 |
| R67Hid | 12.59 | 13.19 |
| R67C | 12.85 | 13.20 |
| R67T | 12.73 | 13.21 |
| R67Q | 12.82 | 13.32 |
| R67N | 12.64 | 13.33 |
| R67V | 13.12 | 13.46 |
| R67M | 12.83 | 13.51 |
| R67L | 13.63 | 13.91 |
| R67I | 13.59 | 14.10 |
| R67Hip | 14.99 | 15.62 |
| R67K | 16.92 | 17.61 |
| R67* | 17.94 | 18.59 |
| T68Q | −12.00 | −11.60 |
| T68R | −8.92 | −8.34 |
| T68E | −2.55 | −2.23 |
| T68K | −2.20 | −1.80 |
| T68M | −0.92 | −0.62 |
| T68I | 2.82 | 2.91 |
| T68Hid | 4.01 | 4.21 |
| T68Hie | 6.16 | 6.38 |
| T68D | 6.54 | 6.74 |
| T68Hip | 7.04 | 7.23 |
| T68V | 10.03 | 10.10 |
| T68N | 11.61 | 11.94 |
| T68G | 14.43 | 14.46 |
| T68A | 14.75 | 14.79 |
| T68C | 14.84 | 14.95 |
| T68S | 14.91 | 15.17 |
| T68* | 16.04 | 16.21 |
| V69Y | −20.72 | −18.18 |
| V69W | −3.45 | −1.01 |
| V69F | −0.74 | 1.54 |
| V69Hie | 17.19 | 19.15 |
| V69E | 18.66 | 19.83 |
| V69Hid | 18.00 | 19.84 |
| V69L | 19.83 | 21.10 |
| V69D | 19.91 | 21.16 |
| V69G | 21.61 | 22.33 |
| V69A | 22.34 | 23.03 |
| V69I | 22.03 | 23.10 |
| V69Hip | 21.19 | 23.32 |
| V69S | 22.33 | 23.37 |
| V69N | 22.27 | 23.43 |
| V69C | 22.79 | 23.61 |
| V69T | 22.76 | 23.70 |
| V69Q | 22.85 | 23.89 |
| V69* | 23.67 | 24.30 |
| V69M | 23.30 | 24.48 |
| V69K | 24.95 | 26.48 |
| V69R | 25.56 | 27.16 |
| N71E | 4.31 | 4.71 |
| N71D | 5.70 | 5.95 |
| N71G | 6.86 | 6.96 |
| N71A | 7.00 | 7.11 |
| N71S | 7.02 | 7.22 |
| N71I | 6.91 | 7.26 |
| N71C | 7.14 | 7.30 |
| N71Hid | 7.05 | 7.32 |
| N71T | 7.18 | 7.46 |
| N71* | 7.25 | 7.49 |
| N71V | 7.43 | 7.60 |
| N71Hie | 7.28 | 7.63 |
| N71F | 7.41 | 7.64 |
| N71W | 7.52 | 7.71 |
| N71Q | 7.33 | 7.72 |
| N71L | 7.62 | 7.74 |
| N71M | 7.63 | 7.96 |
| N71Y | 7.99 | 8.22 |
| N71K | 9.05 | 9.55 |
| N71Hip | 9.23 | 9.59 |
| N71R† | 9.66 | 10.10 |
| R73E | 3.49 | 3.58 |
| R73D | 3.75 | 3.81 |
| R73A | 4.66 | 4.68 |
| R73G | 4.65 | 4.68 |
| R73T | 4.62 | 4.69 |
| R73V | 4.67 | 4.70 |
| R73C | 4.66 | 4.71 |
| R73I | 4.66 | 4.72 |
| R73Hid | 4.66 | 4.73 |
| R73S | 4.64 | 4.73 |
| R73L | 4.66 | 4.73 |
| R73Q | 4.66 | 4.75 |
| R73M | 4.66 | 4.75 |
| R73N | 4.69 | 4.77 |
| R73F | 4.74 | 4.80 |
| R73Y | 4.75 | 4.81 |
| R73Hie | 4.80 | 4.87 |
| R73W | 4.90 | 4.98 |
| R73Hip | 5.93 | 6.01 |
| R73K | 5.90 | 6.04 |
| R73* | 7.99 | 8.09 |
| K84D | 7.60 | 7.71 |
| K84E | 8.03 | 8.22 |
| K84G | 10.42 | 10.47 |
| K84A | 10.45 | 10.53 |
| K84S | 10.53 | 10.73 |
| K84V | 10.69 | 10.75 |

TABLE 4-continued

Table of computational predictions for point mutants in c-Raf-RBD.

| Mutation | Lower Bound log(K*) | Upper Bound log (K*) |
|---|---|---|
| K84T | 10.64 | 10.82 |
| K84I | 10.73 | 10.85 |
| K84C | 10.76 | 10.88 |
| K84N | 10.94 | 11.09 |
| K84Y | 10.91 | 11.15 |
| K84L | 11.16 | 11.29 |
| K84Q | 11.18 | 11.37 |
| K84Hie | 11.34 | 11.50 |
| K84M | 11.27 | 11.51 |
| K84Hid | 11.50 | 11.69 |
| K84F | 12.14 | 12.25 |
| K84W | 12.23 | 12.38 |
| K84Hip | 14.46 | 14.62 |
| K84R | 15.94 | 16.31 |
| K84* | 16.92 | 17.19 |
| A85W | 9.32 | 9.98 |
| A85E | 18.70 | 19.59 |
| A85D | 21.78 | 23.25 |
| A85F | 24.92 | 25.27 |
| A85Q | 24.66 | 25.85 |
| A85Hie | 25.56 | 26.48 |
| A85Y | 25.36 | 26.61 |
| A85C | 25.82 | 26.68 |
| A85N | 25.84 | 26.67 |
| A85* | 26.29 | 26.85 |
| A85G | 26.15 | 26.85 |
| A85T | 26.08 | 27.11 |
| A85S | 26.04 | 27.11 |
| A85M | 26.31 | 27.13 |
| A85Hid | 26.49 | 27.41 |
| A85Hip | 30.10 | 31.04 |
| A85K† | 30.67 | 32.30 |
| A85R | 31.44 | 32.69 |
| K87E | 11.72 | 11.94 |
| K87D | 11.96 | 12.20 |
| K87G | 12.61 | 12.74 |
| K87A | 12.70 | 12.83 |
| K87Q | 12.74 | 12.99 |
| K87S | 12.61 | 13.07 |
| K87C | 12.86 | 13.08 |
| K87M | 12.80 | 13.11 |
| K87W | 12.88 | 13.14 |
| K87V | 12.98 | 13.15 |
| K87N | 12.96 | 13.21 |
| K87I | 13.00 | 13.23 |
| K87T | 12.82 | 13.29 |
| K87L | 13.24 | 13.55 |
| K87Hid | 13.28 | 13.57 |
| K87Hie | 13.33 | 13.59 |
| K87R | 13.55 | 14.11 |
| K87* | 13.42 | 14.14 |
| K87F | 13.99 | 14.15 |
| K87Y† | 14.06 | 14.24 |
| K87Hip | 13.90 | 14.25 |
| V88E | 11.67 | 11.85 |
| V88L | 12.14 | 12.42 |
| V88D | 13.16 | 13.26 |
| V88G | 14.09 | 14.20 |
| V88Q | 14.76 | 14.92 |
| V88A | 14.98 | 15.09 |
| V88S | 15.02 | 15.18 |
| V88M | 15.32 | 15.59 |
| V88C | 15.61 | 15.73 |
| V88I | 15.68 | 15.84 |
| V88N | 15.81 | 15.99 |
| V88T | 15.93 | 16.07 |
| V88* | 16.46 | 16.61 |
| V88Hid | 16.65 | 16.81 |
| V88K | 16.56 | 16.94 |
| V88Hie | 16.83 | 16.96 |
| V88Y† | 17.34 | 17.55 |
| V88Hip | 17.65 | 17.83 |
| V88R | 17.52 | 17.95 |
| V88F† | 17.99 | 18.15 |
| V88W | 18.55 | 18.71 |
| R89Y | −26.90 | −26.05 |
| R89F | −23.87 | −22.50 |
| R89L | 10.43 | 11.19 |
| R89D | 11.43 | 11.88 |
| R89E | 12.74 | 13.18 |
| R89V | 13.77 | 14.23 |
| R89Hid | 13.61 | 14.40 |
| R89G | 14.22 | 14.46 |
| R89A | 14.52 | 14.78 |
| R89T | 13.94 | 14.81 |
| R89S | 14.53 | 15.00 |
| R89N | 14.66 | 15.14 |
| R89C | 15.00 | 15.27 |
| R89Hie | 14.66 | 15.37 |
| R89I | 15.20 | 15.57 |
| R89Q | 16.05 | 16.50 |
| R89Hip | 16.00 | 16.66 |
| R89M | 16.63 | 17.07 |
| R89K | 18.77 | 19.44 |
| R89* | 22.24 | 22.67 |

Each section of the table shows the results of the redesign of a residue position in c-Raf-RBD in the c-Raf-RBD:KRas PPI in order of increasing upper bound on log(K*). The table contains the values for upper and lower bounds on log(K*) values (these bounds are described in detail in [32]). *Design results for the wild-type amino acid identity for each position. †Mutations that were selected for experimental testing and validation.

Experimental Validation of Mutations in the c-Raf-RBD: KRas Protein-Protein Interface:

The mutations selected (highlighted in Table 3) from computational design were experimentally validated using a bio-layer interferometry (BLI) assay. Results from an initial single-concentration BLI screen (see FIG. 9) suggested that, contrary to the computational predictions, the T57K and V88F variants decrease binding, whereas the T57M and K87Y mutations both have a roughly neutral effect on binding, which is consistent with the computational predictions. The final computationally predicted point mutant, V88Y, improves binding a comparable amount to the improvement seen with A85K or N71R, two previously reported variants also predicted by OSPREY and experimentally tested herein that improve binding.

With the discovery of this new variant containing the point mutant V88Y (referred to herein as c-Raf-RBD(Y)) the next step was to combine it with the mutations found in the best reported variant, N71R and A85K (referred to herein as c-Raf-RBD(RK)). Therefore, the double-mutant, c-Raf-RBD(RK), and the new triple-mutant—which contains N71R, A85K, and V88Y and is referred to herein as c-Raf-RBD(RKY)—were also included in the initial BLI screen. Additionally, the c-Raf-RBD(RKY) variant was computationally predicted by FRIES/EWAK* to bind to KRas$^{GTP}$ more tightly than the previous best known binder, c-Raf-RBD(RK) (results are detailed in FIG. 8). Given the promising screening and computational results for the c-Raf-RBD (Y) and c-Raf-RBD(RKY) variants, $K_d$ values for each variant were measured by titrating the analyte over the ligand in a BLI-based assay (see FIG. 10). Excitingly, c-Raf-RBD(RKY) is calculated by the data from the BLI assay (see FIGS. 9 and 10) to bind KRas$^{GTP}$ roughly 5 times better than the previous best known binder, c-Raf-RBD (RK), and approximately 36 times better than wild-type c-Raf-RBD. Given how heavily studied the KRas system is, with several reported mutational and structural studies [48, 64, 65, 67-79], this is a discovery of major significance.

Figure 11:
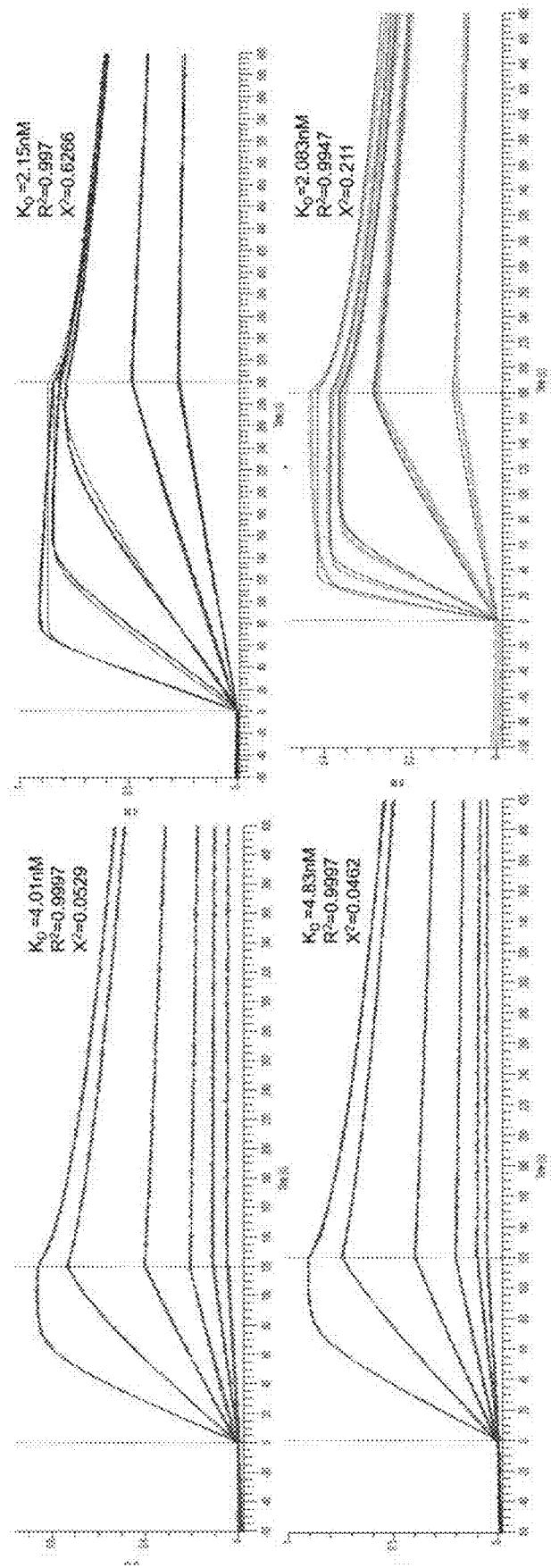
FIG. 11. Replicate BLI titration experiments conducted over different concentration ranges and for different association and dissociation times. Within each titration experiment, curves were fit globally to a mass transport model using the ForteBio Data Analysis HT software. All fits achieved an R2 greater than 0.99 and χ2 smaller than 0.65. The two titration experiments on the left are replicates with concentrations ranging from 150 nM to 4.69 nM in a 2-fold serial dilution. The titration experiment on the top right has titrations ranging from 150 nM to 9.38 nM in a 2-fold serial dilution but with an extended association step. The titration in the bottom right contains binding curves with the following concentrations of c-Raf-RBD(RKY): 200 nM, 125 nM, 75 nM, 75 nM, 25 nM, 25 nM, and 10 nM.

Replicate BLI titration experiments were conducted over different concentration ranges and for different association and dissociation times in order to avoid artifacts. Within each titration experiment, curves were fit globally to a mass transport model using the ForteBio Data Analysis HT software. Results are shown in FIG. 11. All fits achieved an R2 greater than 0.99 and a $\chi^2$ smaller than 0.65. The two titration experiments on the left are replicates with concentrations ranging from 150 nM to 4.69 nM in a 2-fold serial dilution. The titration experiment on the top right has titrations ranging from 150 nM to 9.38 nM in a 2-fold serial dilution but with an extended association step. The titration in the bottom right contains binding curves with the following concentrations of c-Raf-RBD(RKY): 200 nM, 125 nM, 75 nM, 75 nM, 25 nM, 25 nM, and 10 nM. Note the in-experiment repetition of two concentrations (75 nM and 25 nM). This was done in order to control for response and curve shape within an experiment. Curves for the repeat concentrations show strong reproducibility and alternating what repeat curves are used for the global fit changes the Kd within a range of 1.99 nM to 2.34 nM. Results from these four titration experiments were averaged to generate a dissociation constant and standard deviation for c-Raf-RBD (RKY).

Figure 12:
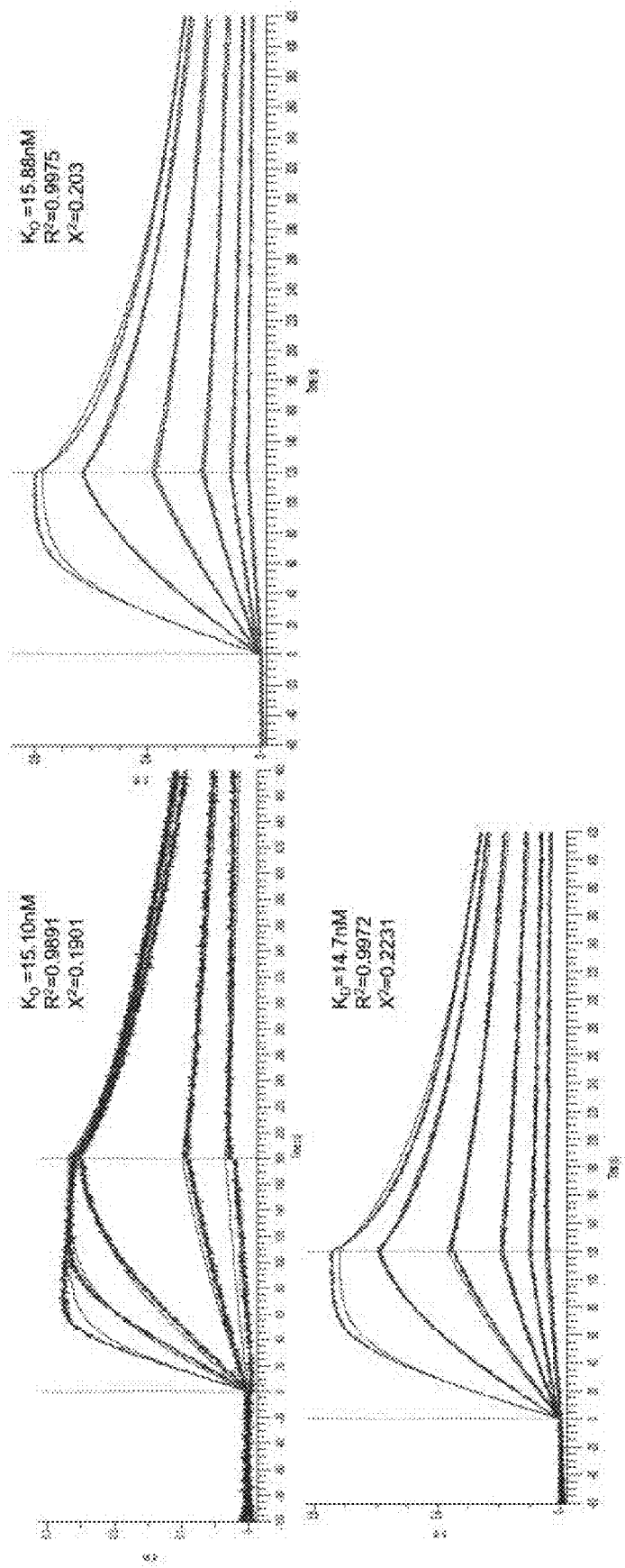
FIG. 12. Additional BLI titration experiments conducted over different concentration ranges and for different association and dissociation times. All fits achieved an R2 greater than 0.98 and a χ2 smaller than 0.25. The titration experiment on the top left was done with the following concentrations of c-Raf-RBD(RK): 200 nM, 125 nM, 75 nM, 75 nM, 25 nM, 25 nM, and 10 nM. Curves for the repeat concentrations show strong reproducibility and alternating what repeat curves are used for the global fit changes the Kd within a range of 15.1 nM to 15.48 nM. The bottom left and top right titration experiments are replicates with concentrations ranging from 150 nM to 4.69 nM in a 2-fold serial dilution. Results from these three titration experiments were averaged to generate a dissociation constant and standard deviation for c-Raf-RBD(RK).

Additional titration experiments were conducted. Results are shown in FIG. 12. All fits achieved an R2 greater than 0.98 and a $\chi^2$ smaller than 0.25. The titration experiment on the top left was done with the following concentrations of c-Raf-RBD(RK): 200 nM, 125 nM, 75 nM, 75 nM, 25 nM, 25 nM, and 10 nM. Note the in-experiment repetition of two concentrations (75 nM and 25 nM). This was done in order to control for response and curve shape within the experiment. Curves for the repeat concentrations show strong reproducibility and alternating what repeat curves are used for the global fit changes the Kd within a range of 15.1 nM to 15.48 nM. The bottom left and top right titration experiments are replicates with concentrations ranging from 150 nM to 4.69 nM in a 2-fold serial dilution. Results from these three titration experiments were averaged to generate a dissociation constant and standard deviation for c-Raf-RBD (RK).

Figure 10:
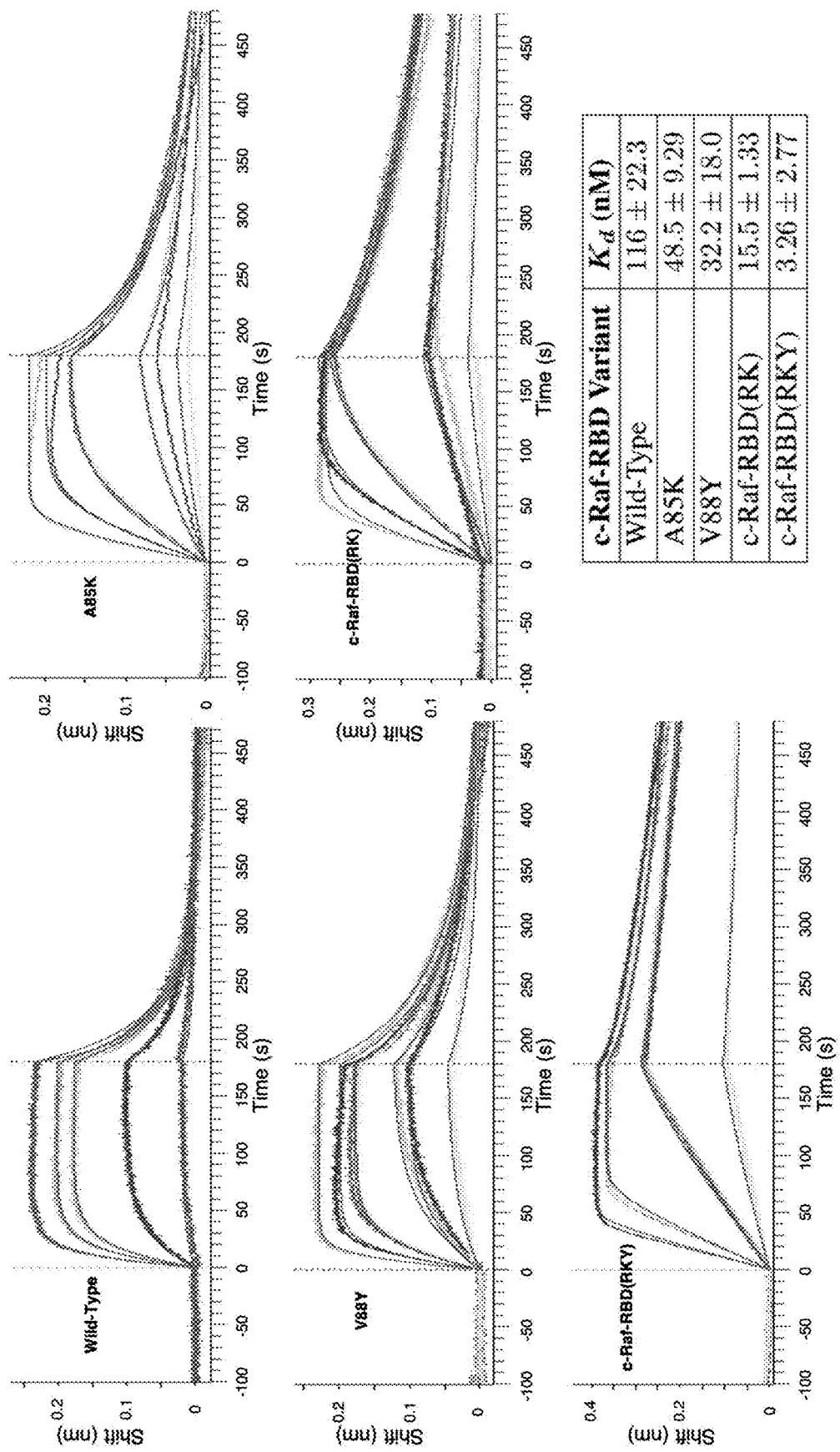
FIG. 10 shows the BLI titration experiments to calculate Kd values for select c-Raf-RBD variants in accordance with one embodiment of the present disclosure. The plots shown here are representative and the data from replicate experiments is presented in Table 5. Each plot shows the data collected from a titration BLI experiment where the concentration of the c-Raf-RBD variant is incrementally increased. The concentrations for the Wild-Type variant were 10, 50, 150, 200, and 300 nM. The concentrations for all of the other variants were 10, 25, 25, 75, 75, 125, and 200 nM. Repeat intermediate concentrations were used as loading controls. These curves were then fit using a mass transport model within the Octet Data Analysis HT software provided by FortéBio in order to calculate the $K_d$ value for each variant's binding to KRas. The values in the table here (bottom right) are average $K_d$ values shown with 2 standard deviations calculated from replicate experiments (see Table 5). The values presented here for Wild-Type, A85K, and c-Raf-RBD(RK) agree well with previously reported $K_d$ values [48]. The best binding variant, c-Raf-RBD(RKY), binds to KRas about 5 times better than the previous tightest-known binder, c-Raf-RBD(RK), and about 36 times better than wild-type c-Raf-RBD.

Materials and Methods:

Bio-Layer Interferometry (BLI) Assay:

Binding of wild-type and variants of c-Raf-RBD were experimentally measured using a bio-layer interferometry (BLI) assay. Each variant of c-Raf-RBD was expressed and purified (see SI Text 8.1) with cysteine residues at positions 81 and 96 substituted for isoleucine and methionine, respectively. These mutations were previously reported to have a minimal effect on the stability of c-Raf-RBD [73] and their substitution allows for the use of the c-Raf-RBD constructs in other assays. Additionally, these residue substitutions are not believed to have a large effect since the $K_d$ values determined herein align with previously reported $K_d$ values [48] (see FIG. 10). KRas was expressed and purified (see SI Text 8.2) with a poly-histidine protein tag (His-tag) and loaded with a non-hydrolyzable GTP analog, GppNHp. KRas was also made to include a substitution at position 118 from cysteine to serine in order to increase expression and stability [80]. Ni-NTA tips were then used to perform the BLI experiments to determine binding of the c-Raf-RBD variants to KRas$^{GppNHp}$ (results are shown in FIGS. 9 and 10 and Table 5). All experiments were carried out in 30 mM phosphate pH 7.4, 327 mM NaCl, 2.7 mM KCl, 5 mM MgCl$_2$, 1.5 mM TCEP, 0.1% BSA, and 0.02% Tween-20+ Kathon at 25° C. with 1000 RPM shaking and a KRas loading concentration of 20 µg/ml. Each curve presented (see FIGS. 9 and 10) was fit using the built-in mass transport model within the Octet Data Analysis HT software provided by ForteBio. Fits with a sum of square deviations $\chi^2$ less than 1 (ForteBio recommends a value less than 3) and a coefficient of determination R2 greater than 0.98 were accepted.

TABLE 5

$K_d$ values for each tested variant for all replicates of BLI titration experiments.

| Run | Variant | Kd | $\chi^2$ | R$^2$ |
|---|---|---|---|---|
| 1 | c-Raf-RBD(RKY) | 4.83 × 10$^{-9}$ | 0.0462 | 0.9997 |
| 2 | c-Raf-RBD(RKY) | 4.01 × 10$^{-9}$ | 0.0529 | 0.9997 |
| 3 | c-Raf-RBD(RKY) | 2.04 × 10$^{-9}$ | 0.211 | 0.9947 |
| 4 | c-Raf-RBD(RKY) | 2.15 × 10$^{-9}$ | 0.6266 | 0.997 |
| 1 | c-Raf-RBD(RK) | 1.47 × 10$^{-8}$ | 0.2232 | 0.9972 |
| 2 | c-Raf-RBD(RK) | 1.59 × 10$^{-8}$ | 0.2303 | 0.9975 |
| 3 | c-Raf-RBD(RK) | 1.58 × 10$^{-8}$ | 0.2269 | 0.9895 |
| 1 | A85K | 5.18 × 10$^{-8}$ | 0.3814 | 0.9957 |
| 2 | A85K | 4.53 × 10$^{-8}$ | 0.1414 | 0.9885 |
| 1 | V88Y | 3.86 × 10$^{-8}$ | 0.7742 | 0.9914 |
| 2 | V88Y | 2.59 × 10$^{-8}$ | 0.1658 | 0.9898 |
| 1 | Wild-Type | 1.31 × 10$^{-7}$ | 0.0971 | 0.9938 |
| 2 | Wild-Type | 1.01 × 10$^{-7}$ | 0.2561 | 0.9917 |
| 3 | Wild-Type | 1.17 × 10$^{-7}$ | 0.4417 | 0.9856 |

For each listed variant, the dissociation constant $K_d$ is given for each BLI titration experiment calculated from the fit done using the built-in mass transport model within the Octet Data Analysis HT software provided by ForteBio. Only fits with a sum of square deviations $\chi^2$ less than 1 (ForteBio recommends a value less than 3) and a coefficient of determination R$^2$ greater than 0.98 were accepted. Presented in the table in FIG. 10 are averages of these $K_d$ values.

Homology Model of c-Raf-RBD in Complex with KRas:

PDB ID 4DSN [81] is an X-ray crystal structure of KRas isoform 2B which contains G12D, a mutation that locks KRas into its active form. This structure of KRas bound to a GTP analog was used to model KRas$^{GTP}$. PDB ID 1GUA [67] is an X-ray crystal structure of c-Raf in complex with Rap, a Ras homolog. These two structures (4DSN and 1GUA) were aligned using PyMol [82]. Rap was then removed, leaving c-Raf poised in complex with KRas from PDB ID 4DSN. This complex was then minimized using Sander from AmberTools for 200 steps [83] to relax any steric clashes.

Experimental Preparation and Validation of c-Raf-RBD Variants and KRas:

Expression and Purification of c-Raf-RBD Variants:

The c-Raf-RBD variants were made in a C81I, C96M background (as described in Section 5.3.1). Each c-Raf-RBD variant was expressed with a N-term His-SUMO tag to increase expression and facilitate purification. Variants were then grown to an OD600 of 0.8 at 37° C. in Rosetta 2(DE3) cells in LB media with kanamycin and chloramphenicol. Cells were then induced with 1 mM IPTG at 16° C. overnight. Cells were then pelleted, re-suspended in Lysis Buffer (40 mM Tris-HCl, 50 mM NaCl, 5 mM MgCl$_2$, 5 mM CaCl$_2$), and 1 mM TCEP at pH 8.0 with 1 mM PMSF), and lysed with 5 passages through a homo-fluidizer. Next, the lysate was incubated with 5 µl of micrococcal nuclease (stock concentration of 2,000,000 gel units/ml) per liter of cell growth for 20 minutes at 37° C. The lysate was centrifuged and the supernatant was then loaded onto a nickel NTA column in lysis buffer and eluted with a gradient from 0-100% Buffer B (40 mM Tris-HCl, 500 mM NaCl, 5 mM MgCl$_2$, 500 mM Imidazole, and 1 mM TCEP at pH 7.4). Fractions of interest were collected, concentrated (10 kDa MWCO), and buffer exchanged through a G-25 Sephadex column into Protease Buffer (40 mM Tris-HCl and 250 mM NaCl at pH 8.0). Each c-Raf-RBD variant was then concentrated and incubated with 3 mg of SUMO protease (roughly 1 mg per 10 mg of SUMO-labeled c-Raf-RBD) at 30° C. overnight to cleave the His-SUMO tag. Each variant was then loaded onto a nickel NTA column in Protease Buffer and eluted with a gradient from 0-100% Buffer B. Flow-through was collected, concentrated, and buffer exchanged through a G-25 Sephadex column into 50 mM phosphate at pH 6.5. Desalted variants were then further purified with a cation exchange SP Sepharose column eluted with 50 mM phosphate, 500 mM NaCl, and 5 mM TCEP at pH 6.5. Each c-Raf-RBD variant was then concentrated (3 kDa MWCO) and buffer exchanged into 40 mM Tris-HCl, 250 mM NaCl, 5 mM MgCl$_2$, and 1 mM TCEP at pH 7.4. The purity of each variant was determined by SDS-PAGE gel (data not shown) and further identified by matrix assisted laser desorption ionization time of flight (MALDI-TOF) mass spectrometry (data not shown).

Expression and Purification of KRas:

KRas was made with a N-term His-tag in a C118S background, which was introduced to increase expression and stability (see Section 5.3.1). KRas was grown to an OD600 of 0.8 at 37° C. in Rosetta 2(DE3) cells in LB media with kanamycin and chloramphenicol. Cells were then induced with 1 mM IPTG and incubated 37° C. for 5 hours before being lowered to 16° C. overnight. Cells were then pelleted, re-suspended in Lysis Buffer (40 mM Tris-HCl, 50 mM NaCl, 5 mM MgCl$_2$, 5 mM CaCl$_2$), and 1 mM TCEP at pH 8.0 with 1 mM PMSF) and then lysed with 5 passages through a homo-fluidizer. Next, the lysate was incubated with 5 µl of micrococcal nuclease (stock concentration of 2,000,000 gel units/ml) per liter of cell growth for 20 minutes at 37° C. The lysate was centrifuged and the supernatant was then loaded onto a nickel NTA column in lysis buffer and eluted with a gradient from 0-100% Buffer B (40 mM Tris-HCl, 500 mM NaCl, 5 mM MgCl$_2$, 500 mM Imidazole, and 1 mM TCEP at pH 7.4). Fractions of interest were collected, concentrated (10 kDa MWCO), and buffer exchanged through a G-25 Sephadex column into Desalting Buffer (50 mM Tris-HCl and 50 mM NaCl at pH 8.0). Then, KRas was concentrated (10 kDa MWCO) in preparation for nucleotide loading. The Desalting Buffer was then supplemented with 200 mM ammonium sulphate, 1 UM zinc chloride, 50 units of calf intestinal phosphatase (CIP), and 10 molar excess of a non-hydrolysable GTP analogue guanosine-5'-[(β,γ)-imido]triphosphate (GppNHp). KRas was incubated with GppNHp for 2 hours at room temperature and then overnight at 4° C. The reaction was terminated by the addition of 60 mM MgCl$_2$. Next, KRas$^{GppNHp}$ was loaded onto a Superdex 75 column in 40 mM Tris-HCl, 250 mM NaCl, 5 mM MgCl$_2$, and 1 mM TCEP at pH 7.4. Purity was confirmed by SDS-PAGE gel (data not shown) and GppNHp loading was confirmed by high-performance anion exchange chromatography (HPAEC, data not shown).

Discussion:

FRIES and EWAK* are new, provable algorithms for more efficient ensemble-based computational protein design. Efficiency and efficacy were tested and shown across a total of 2.826 different design problems. An implementation of FRIES/EWAK* is available in the open-source protein design software OSPREY [1] and all of the data has been made available (see Data Availability Statement). FRIES/EWAK* in combination achieved a significant runtime improvement over the previous state-of-the-art, BBK*, with runtimes up to 2 orders of magnitude faster. EWAK* also limits the number of minimized conformations used in each K* score approximation by up to about 2 orders of magnitude while maintaining provable guarantees (see Section 3.1.2). FRIES alone is capable of reducing the input sequence space while provably keeping all of the most energetically favorable sequences (see Section 3.1.1), decreasing the size of the sequence space by more than 2 orders of magnitude, and leading to more efficient design given the smaller search space.

To further validate OSPREY with FRIES/EWAK*, these algorithms were applied to a biomedically significant design problem: the c-Raf-RBD:KRas PPI. First, a series of retrospective designs were performed where FRIES/EWAK* accurately predicted how a variety of mutations affect the binding of c-Raf-RBD to KRas$^{GTP}$ that previous computational methods had failed to accurately predict [48]. This success supports the use of OSPREY and FRIES/EWAK* to evaluate the affect mutations in the protein-protein interface of c-Raf-RBD:KRas have on binding (more, similar successes of the K* algorithm are presented and discussed in [1]). FRIES/EWAK* also prospectively predicted the effect of new mutations in the c-Raf-RBD:KRas PPI and discovered a novel c-Raf-RBD mutation V88Y with improved affinity for KRas. This new mutation was combined with two previously reported mutations, N71R and A85K [48], to create c-Raf-RBD(RKY), an even stronger binding c-Raf-RBD variant, which FRIES/EWAK* accurately predicted. Top predicted variants were screened using an initial biolayer interferometry (BLI) single-concentration assay. Only a promising subset of the computationally predicted and initially screened variants were then evaluated using a BLI titration assay to calculate K$_d$ values for individual c-Raf-RBD variants. It was determined that c-Raf-RBD(RKY) binds to KRas$^{GTP}$ roughly 36 times more tightly than wild-type c-Raf-RBD, making it the tightest known c-Raf-RBD variant binding partner of KRas$^{GTP}$ Given that numerous groups have explored this protein-protein interaction [64, 65, 67-77] and performed mutagenesis on c-Raf-RBD either, through rational means [64, 67, 74, 78], computational methods [48, 65] or high-throughput evolutionary methods [73, 79] and that none identified V88Y, this discovery validates the computational approach and the use of computational algorithms such as FRIES and EWAK* to re-design protein-protein interfaces toward improved binding. Additionally, previous mutations that enhanced the affinity of c-Raf-RBD to KRas did so by supercharging c-Raf-RBD [48, 64, 65]. In contrast, the mutation V88Y introduces a novel, aromatic residue. The discovery that such a mutation can improve the binding of c-Raf-RBD to KRas$^{GTP}$ is of considerable significance. These new c-Raf-RBD variants serve as an important step toward better understanding the KRas:effector interface and eventually developing successful therapeutics to directly target and block the aberrant behavior of mutant KRas.

REFERENCES

[1] M. A. Hallen, J. W. Martin, A. Ojewole, J. D. Jou, A. U. Lowegard, M. S. Frenkel, P. Gainza, H. M. Nisonoff, A. Mukund, S. Wang, G. T. Holt, D. Zhou, E. Dowd, and B. R. Donald. OSPREY 3.0: open-source protein redesign for you, with powerful new features.

*Journal of Computational Chemistry*, 39(30):2494-2507, 2018. DOI: 10.1002/jcc.25522.

[2] A. Ojewole, A. Lowegard, P. Gainza, S. M. Reeve, I. Georgiev, A. C. Anderson, and B. R. Donald. OSPREY predicts resistance mutations using positive and negative computational protein design. In *Computational Protein Design*, part 15, pages 291-306. Springer, 2017.

[3] P. Gainza, K. E. Roberts, I. Georgiev, R. H. Lilien, D. A. Keedy, C.-Y. Chen, F. Reza, A. C. Anderson, D. C. Richardson, J. S. Richardson, and B. R. Donald. OSPREY: protein design with ensembles, flexibility, and provable algorithms. *Methods Enzymol*, 523:87-107, 2013.

[4] B. R. Donald. *Algorithms in Structural Molecular Biology*. MIT Press, Cambridge, M A, 2011.

[5] P. Gainza, H. M. Nisonoff, and B. R. Donald. Algorithms for protein design. *Current Opinion in Structural Biology*, 39:16-26, 2016.

[6] D. Simoncini, D. Allouche, S. d. Givry, C. Delmas, S. Barbe, and T. Schiex. Guaranteed discrete energy optimization on large protein design problems. *J Chem Theory Comput*, 11(12):5980-9, 2015.

[7] M. A. Hallen and B. R. Donald. Protein design by algorithm. arXiv preprint arXiv: 1806.06064, 2018.

[8] B Kuhlman and D Baker. Native protein sequences are close to optimal for their structures. *Proc Natl Acad Sci USA*, 97(19):10383-8, 2000.

[9] A. Leaver-Fay, et al. Rosetta3: anobject-oriented software suite for the simulation and design of macromolecules. *Methods Enzymol*, 487:545-74, 2011.

[10] C. Lee and S. Subbiah. Prediction of protein side-chain conformation by packing optimization. eng. *Journal of Molecular Biology*, 217(2):373-388, 1991. ISSN: 0022-2836.

[11] S. C. Lovell, J. M. Word, J. S. Richardson, and D. C. Richardson. The penultimate rotamer library. *Proteins*, 40(3):389-408, 2000.

[12] I. Georgiev, R. H. Lilien, and B. R. Donald. The minimized dead-end elimination criterion and its application to protein redesign in a hybrid scoring and search algorithm for computing partition functions over molecular ensembles. *J Comput Chem*, 29(10): 1527-42, 2008.

[13] P. Gainza, K. E. Roberts, and B. R. Donald. Protein design using continuous rotamers. *PLOS Comput Biol*, 8(1):e1002335, 2012.

[14] M. A. Hallen, P. Gainza, and B. R. Donald. Compact representation of continuous energy surfaces for more efficient protein design. *J Chem Theory Comput*, 11(5): 2292-306, 2015.

[15] M. A. Hallen, J. D. Jou, and B. R. Donald. LUTE (local unpruned tuple expansion): accurate continuously flexible protein design with general energy functions and rigid-rotamer-like efficiency. *Research in Computational Molecular Biology (RECOMB)*, 9649:122-136, 2016.

[16] I. Georgiev and B. R. Donald. Dead-end elimination with backbone flexibility. *Bioinformatics*, 23(13):i185-94, 2007.

[17] I. Georgiev, D. Keedy, J. S. Richardson, D. C. Richardson, and B. R. Donald. Algorithm for backrub motions in protein design. *Bioinformatics*, 24(13):1196-204, 2008.

[18] M. A. Hallen and B. R. Donald. CATS (coordinates of atoms by taylor series): protein design with backbone flexibility in all locally feasible directions. *Bioinformatics*, 33(14):15-i12, 2017.

[19] M. A. Hallen, D. A. Keedy, and B. R. Donald. Dead-end elimination with perturbations (DEEPer): a provable protein design algorithm with continuous sidechain and backbone flexibility. *Proteins*, 81(1):18-39, 2013.

[20] S.-R. Tzeng and C. G. Kalodimos. Protein activity regulation by conformational entropy. *Nature*, 488(7410): 236, 2012.

[21] M. K. Gilson, J. A. Given, B. L. Bush, and J. A. McCammon. The statistical-thermodynamic basis for computation of binding affinities: a critical review. *Biophys J*, 72(3): 1047-69, 1997.

[22] C.-Y. Chen, I. Georgiev, A. C. Anderson, and B. R. Donald. Computational structure-based redesign of enzyme activity. *Proc Natl Acad Sci USA*, 106(10):3764-9, 2009.

[23] D. Sciretti, P. Bruscolini, A. Pelizzola, M. Pretti, and A. Jaramillo. Computational protein design with side-chain conformational entropy. *Proteins*, 74(1): 176-91, 2009.

[24] I. Georgiev, R. H. Lilien, and B. R. Donald. Improved pruning algorithms and divide-and-conquer strategies for dead-end elimination, with application to protein design. *Bioinformatics*, 22(14):e174-83, 2006.

[25] B. I. Dahiyat and S. L. Mayo. De novo protein design: fully automated sequence selection. *Science*, 278(5335): 82-7, 1997.

[26] A. R. Leach and A. P. Lemon. Exploring the conformational space of protein side chains using dead-end elimination and the A* algorithm. *Proteins*, 33(2):227-39, 1998.

[27] S. Traoré, D. Allouche, I. André, S. d. Givry, G. Katsirelos, T. Schiex, and S. Barbe. A new framework for computational protein design through cost function network optimization. *Bioinformatics*, 29(17):2129-36, 2013.

[28] M. S. Bernard Chazelle C. K. A semidefinite programming approach to side chain positioning with new rounding strategies. *N FORMS JOURNAL ON COMPUTING*, 16(4):380-392, 2004.

[29] R. H. Lilien, B. W. Stevens, A. C. Anderson, and B. R. Donald. A novel ensemble-based scoring and search algorithm for protein redesign and its application to modify the substrate specificity of the gramicidin synthetase a phenylalanine adenylation enzyme. *J Comput Biol*, 12(6): 740-61, 2005.

[30] K. E. Roberts, P. R. Cushing, P. Boisguerin, D. R. Madden, and B. R. Donald. Computational design of a PDZ domain peptide inhibitor that rescues CFTR activity. *PLOS Comput Biol*, 8(4):e1002477, 2012.

[31] N. W. Silver, B. M. King, M. N. L. Nalam, H. Cao, A. Ali, G. S. Kiran Kumar Reddy, T. M. Rana, C. A. Schiffer, and B. Tidor. Efficient computation of small-molecule configurational binding entropy and free energy changes by ensemble enumeration. *J Chem Theory Comput*, 9(11): 5098-5115, 2013.

[32] A. A. Ojewole, J. D. Jou, V. G. Fowler, and B. R. Donald. BBK* (*branch and bound over K**): *a provable and efficient ensemble-based algorithm to optimize stability and binding affinity over large sequence spaces*. In Springer International Publishing, 2017, pages 157-172.

[33] C. Viricel, D. Simoncini, S. Barbe, and T. Schiex. Guaranteed weighted counting for affinity computation: beyond determinism and structure. In *International Conference on Principles and Practice of Constraint Programming*, pages 733-750. Springer, 2016.

[34] S. Traoré, D. Allouche, I. André, T. Schiex, and S. Barbe. Deterministic search methods for computational protein design. *Methods Mol Biol*, 1529:107-123, 2017.

[35] S. Traoré, K. E. Roberts, D. Allouche, B. R. Donald, I. André, T. Schiex, and S. Barbe. Fast search algorithms for computational protein design. *J Comput Chem*, 37(12): 1048-58, 2016.

[36] B. W. Stevens, R. H. Lilien, I. Georgiev, B. R. Donald, and A. C. Anderson. Redesigning the PheA domain of gramicidin synthetase leads to a new understanding of the enzyme's mechanism and selectivity. *Biochemistry*, 45(51):15495-504, 2006.

[37] K. M. Frey, I. Georgiev, B. R. Donald, and A. C. Anderson. Predicting resistance mutations using protein design algorithms. *Proc Natl Acad Sci USA*, 107(31): 13707-12, 2010.

[38] S. M. Reeve, P. Gainza, K. M. Frey, I. Georgiev, B. R. Donald, and A. C. Anderson. Protein design algorithms predict viable resistance to an experimental antifolate. *Proc Natl Acad Sci USA*, 112(3):749-54, 2015.

[39] M. J. Gorczynski, J. Grembecka, Y. Zhou, Y. Kong, L. Roudaia, M. G. Douvas, M. Newman, I. Bielnicka, G. Baber, T. Corpora, J. Shi, M. Sridharan, R. Lilien, B. R. Donald, N. A. Speck, M. L. Brown, and J. H. Bushweller. Allosteric inhibition of the protein-protein interaction between the leukemia-associated proteins Runx1 and CBFbeta. *Chem Biol*, 14(10):1186-97, 2007.

[40] I. Georgiev, S. Schmidt, Y.Li, D. Wycuff, G. Ofek, N. Doria-Rose, T. Luongo, Y. Yang, T. Zhou, B. R. Donald, J. Mascola, and P. Kwong. Design of epitope-specific probes for sera analysis and antibody isolation. Retrovirology, 9, 2012.

[41] I. S. Georgiev, R. S. Rudicell, K. O. Saunders, W. Shi, T. Kirys, K. McKee, S. O'Dell, G.-Y. Chuang, Z.-Y. Yang, G. Ofek, M. Connors, J. R. Mascola, G. J. Nabel, and P. D. Kwong. Antibodies VRC01 and 10E8 neutralize HIV-1 with high breadth and potency even with IG-framework regions substantially reverted to germline. *J Immunol*, 192(3):1100-6, 2014.

[42] R. S. Rudicell et al. Enhanced potency of a broadly neutralizing HIV-1 antibody in vitro improves protection against lentiviral infection in vivo. *J Virol*, 88(21): 12669-82, 2014.

[43] A phase 1, single dose study of the safety and virologic effect of an HIV-1 specific broadly neutralizing human monoclonal antibody, VRC-HIVMAB080-00-AB (VRC01LS) or VRC-HIVMAB075-00-AB (VRC07-523LS), administered intravenously to HIV-infected adults. clinicaltrials.gov identifier: nct02840474. niaid and national institutes of health clinical center. September (2018).

[44] Evaluating the safety and serum concentrations of a human monoclonal antibody, VRC-HIVMAB075-00-AB (VRC07-523LS), administered in multiple doses and routes to healthy, HIV-uninfected adults. clinicaltrials.gov identifier: nct03387150. niaid and national institutes of health clinical center. September (2018).

[45] VRC 610: phase i safety and pharmacokinetics study to evaluate a human monoclonal antibody (MAB) VRC-HIVMAB095-00-AB (10E8VLS) administered alone or concurrently with MAB VRC-HIVMAB075-00-AB (VRC07-523LS) via subcutaneous injection in healthy adults. clinicaltrials.gov identifier: nct03565315.

[46] B. Kuhlman and D. Baker. Native protein sequences are close to optimal for their structures. *Proceedings of the National Academy of Sciences*, 97(19): 10383-10388, 2000.

[47] B. Papke and C. J. Der. Drugging RAS: know the enemy. Science, 355(6330):1158-1163, 2017.

[48] D. Filchtinski, O. Sharabi, A. Rüppel, I. R. Vetter, C. Herrmann, and J. M. Shifman. What makes Ras an efficient molecular switch: a computational, biophysical, and structural study of Ras-GDP interactions with mutants of Raf. *Journal of molecular biology*, 399(3): 422-435, 2010.

[49] J. Lee. New Monte Carlo algorithm: entropic sampling. *Physical Review Letters*, 71(2):211, 1993.

[50] S. Nosé. A molecular dynamics method for simulations in the canonical ensemble. *Molecular physics*, 52(2):255-268, 1984.

[51] W. K. Hastings. Monte carlo sampling methods using markov chains and their applications. *Biometrika*, 1970.

[52] Q. Lou, R. Dechter, and A. T. Ihler. Dynamic importance sampling for anytime bounds of the partition function. In *Advances in Neural Information Processing Systems*, pages 3196-3204, 2017.

[53] K. E. Roberts, P. Gainza, M. A. Hallen, and B. R. Donald. Fast gap-free enumeration of conformations and sequences for protein design. *Proteins*, 83(10): 1859-77, 2015.

[54] R. Sommer, S. Wagner, A. Varrot, C. M. Nycholat, A. Khaledi, S. Häussler, J. C. Paulson, A. Imberty, and A. Titz. The virulence factor LecB varies in clinical isolates: consequences for ligand binding and drug discovery. *Chemical Science*, 7(8):4990-5001, 2016.

[55] M. A. Hallen and B. R. Donald. COMETS (constrained optimization of multistate energies by tree search): a provable and efficient protein design algorithm to optimize binding affinity and specificity with respect to sequence. *Journal of Computational Biology*, 23(5):311-321, 2016.

[56] J. D. Jou, G. T. Holt, A. U. Lowegard, and B. R. Donald. Minimization-aware recursive K* (MARK*): a novel, provable algorithm that accelerates ensemble-based protein design and provably approximates the energy landscape. In *International Conference on Research in Computational Molecular Biology*, pages 101-119. Springer, 2019.

[57] J. M. Ostrem, U. Peters, M. L. Sos, J. A. Wells, and K. M. Shokat. K-Ras (G12C) inhibitors allosterically control GTP affinity and effector interactions. *Nature*, 503(7477): 548, 2013.

[58] J. C. Hunter, D. Gurbani, S. B. Ficarro, M. A. Carrasco, S. M. Lim, H. G. Choi, T. Xie, J. A. Marto, Z. Chen, N. S. Gray, et al. In situ selectivity profiling and crystal structure of SML-8-73-1, an active site inhibitor of oncogenic K-Ras G12C. *Proceedings of the National Academy of Sciences*, 111(24): 8895-8900, 2014.

[59] P. Lito, M. Solomon, L.-S. Li, R. Hansen, and N. Rosen. Allele-specific inhibitors inactivate mutant KRAS G12C by a trapping mechanism. *Science*, 351(6273):604-608, 2016.

[60] M. P. Patricelli, M. R. Janes, L.-S. Li, R. Hansen, U. Peters, L. V. Kessler, Y. Chen, J. M. Kucharski, J. Feng, T. Ely, et al. Selective inhibition of oncogenic KRAS output with small molecules targeting the inactive state. *Cancer discovery*, 6(3):316-329, 2016.

[61] M. Zeng, J. Lu, L. Li, F. Feru, C. Quan, T. W. Gero, S. B. Ficarro, Y. Xiong, C. Ambrogio, R. M. Paranal, et al. Potent and selective covalent quinazoline inhibitors of KRAS G12C. *Cell chemical biology*, 24(8): 1005-1016, 2017.

[62] M. R. Janes, J. Zhang, L.-S. Li, R. Hansen, U. Peters, X. Guo, Y. Chen, A. Babbar, S. J. Firdaus, L. Darjania, et al. Targeting KRAS mutant cancers with a covalent G12C-specific inhibitor. *Cell*, 172(3):578-589, 2018.

[63] M. Fakih, B. O'Neil, T. J. Price, G. S. Falchook, J. Desai, J. Kuo, R. Govindan, E. Rasmussen, P. K. H. Morrow, J. Ngang, et al. Phase 1 study evaluating the safety, tolerability, pharmacokinetics (PK), and efficacy of AMG 510, a novel small molecule KRASG12C inhibitor, in advanced solid tumors. 2019.

[64] M. Fridman, H. Maruta, J. Gonez, F. Walker, H. Treutlein, J. Zeng, and A. Burgess. Point mutants of c-raf-1 RBD with elevated binding to v-Ha-Ras. *Journal of Biological Chemistry*, 275(39):30363-30371, 2000.

[65] C. Kiel, D. Filchtinski, M. Spoerner, G. Schreiber, H. R. Kalbitzer, and C. Herrmann. Improved binding of Raf to Ras GDP is correlated with biological activity. *Journal of Biological Chemistry*, 284(46):31893-31902, 2009.

[66] K. E. Roberts. Http://www.cs.duke.edu/donaldlab/software/proteininteractionviewer/. *Protein Interaction Viewer*, 2012.

[67] N. Nassar, G. Horn, C. Herrmann, C. Block, R. Janknecht, and A. Wittinghofer. Ras/Rap effector specificity determined by charge reversal. *Nature Structural and Molecular Biology*, 3(8):723, 1996.

[68] J. R. Sydor, R. P. Seidel, R. S. Goody, and M. Engelhard. Cell-free synthesis of the ras-binding domain of c-Raf-1: binding studies to fluorescently labelled H-Ras. *FEBS letters*, 452(3):375-378, 1999.

[69] C. Herrmann, G. Horn, M. Spaargaren, and A. Wittinghofer. Differential interaction of the ras family GTP-binding proteins H-Ras, Rap1A, and R-Ras with the putative effector molecules Raf kinase and Ral-guanine nucleotide exchange factor. *Journal of Biological Chemistry*, 271(12):6794-6800, 1996.

[70] C. Herrmann, G. A. Martin, and A. Wittinghofer. Quantitative analysis of the complex between p21 and the ras-binding domain of the human raf-1 protein kinase. *Journal of Biological Chemistry*, 270(7): 2901-2905, 1995.

[71] B. Lakshman, S. Messing, E. M. Schmid, J. D. Clogston, W. K. Gillette, D. Esposito, B. Kessing, D. A. Fletcher, D. V. Nissley, F. McCormick, et al. Quantitative biophysical analysis defines key components modulating recruitment of the GTPase KRAS to the plasma membrane. *Journal of Biological Chemistry*, 294(6):2193-2207, 2019.

[72] C. Block, R. Janknecht, C. Herrmann, N. Nassar, and A. Wittinghofer. Quantitative structure-activity analysis correlating Ras/Raf interaction in vitro to Raf activation in vivo. *Nature structural biology*, 3(3):244, 1996.

[73] F.-X. Campbell-Valois, K. Tarassov, and S. Michnick. Massive sequence perturbation of the Raf Ras binding domain reveals relationships between sequence conservation, secondary structure propensity, hydrophobic core organization and stability. *Journal of molecular biology*, 362(1):151-171, 2006.

[74] M. Fridman, F. Walker, B. Catimel, T. Domagala, E. Nice, and A. Burgess. c-Raf-1 RBD associates with a subset of active vH-Ras. *Biochemistry*, 39(50):15603-15611, 2000.

[75] S. K. Fetics, H. Guterres, B. M. Kearney, G. Buhrman, B. Ma, R. Nussinov, and C. Mattos. Allosteric effects of the oncogenic RasQ61L mutant on Raf-RBD. *Structure*, 23(3):505-516, 2015.

[76] C. Gorman, R. H. Skinner, J. V. Skelly, S. Neidle, and P. N. Lowe. Equilibrium and kinetic measurements reveal rapidly reversible binding of Ras to Raf. *Journal of Biological Chemistry*, 271(12):6713-6719, 1996.

[77] J. C. Hunter, A. Manandhar, M. A. Carrasco, D. Gurbani, S. Gondi, and K. D. Westover. Biochemical and structural analysis of common cancer-associated KRAS mutations. *Molecular cancer research*, 13(9):1325-1335, 2015.

[78] M. Fridman, A. Tikoo, M. Varga, A. Murphy, M. Nur-E-Kamal, and H. Maruta. The minimal fragments of c-Raf-1 and NF1 that can suppress v-Ha-Ras-induced malignant phenotype. *Journal of Biological Chemistry*, 269(48):30105-30108, 1994.

[79] F.-X. Campbell-Valois, K Tarassov, and S. Michnick. Massive sequence perturbation of a small protein. *Proceedings of the National Academy of Sciences*, 102(42): 14988-14993, 2005.

[80] Q. Sun, J. P. Burke, J. Phan, M. C. Burns, E. T. Olejniczak, A. G. Waterson, T. Lee, O. W. Rossanese, and S. W. Fesik. Discovery of small molecules that bind to K-Ras and inhibit Sos-mediated activation. *Angewandte Chemie International Edition*, 51(25):6140-6143, 2012.

[81] T. Maurer, L. S. Garrenton, A. Oh, K. Pitts, D. J. Anderson, N. J. Skelton, B. P. Fauber, B. Pan, S. Malek, D. Stokoe, et al. Small-molecule ligands bind to a distinct pocket in Ras and inhibit sos-mediated nucleotide exchange activity. *Proceedings of the National Academy of Sciences*, 109(14):5299-5304, 2012.

[82] W. L. DeLano. The PyMOL molecular graphics system. http://www.pymol.org, 2002.

[83] D. Pearlman, D. Case, J. Caldwell, W. Ross, T. Cheatham, S DeBolt, D Ferguson, G Seibel, and P Kollman. AMBER: a package of computer programs for applying molecular mechanics, normal mode analysis, molecular dynamics and free energy calculations to simulate the structural and energetic properties of molecules. *Comput Phys Commun*, 91(42): 1-41, 1995.

What is claimed is:

1. A RAF proto-oncogene serine/threonine-protein kinase (c-RAF) Ras binding domain (RBD) variant containing exactly three substitution mutations relative to a wildtype human c-RAF RBD sequence, wherein the three mutations are V88Y, N71R, and A85K.

2. A polynucleotide encoding the c-RAF RBD variant of claim 1.

3. A conjugate comprising the c-RAF RBD variant of claim 1.

4. The conjugate of claim 3, comprising a cell targeting moiety, a cell penetrating moiety, or a combination thereof.

* * * * *